US009738709B2

(12) United States Patent
Kuret et al.

(10) Patent No.: US 9,738,709 B2
(45) Date of Patent: Aug. 22, 2017

(54) METHYLATED PEPTIDES DERIVED FROM TAU PROTEIN AND THEIR ANTIBODIES FOR DIAGNOSIS AND THERAPY OF ALZHEIMER'S DISEASE

(71) Applicants: Ohio State Innovation Foundation, Columbus, OH (US); University of Maryland, Baltimore, Baltimore, MD (US)

(72) Inventors: Jeffrey A. Kuret, Dublin, OH (US); Kristen E. Funk, St. Louis, MO (US); Jyanyu Austin Yang, Columbia, MD (US); Stefani Thomas, Parkville, MD (US)

(73) Assignees: Ohio State Innovation Foundation, Columbus, OH (US); University of Maryland, Baltimore, Baltimore, MD (US)

( * ) Notice: Subject to any disclaimer, the term of this patent is extended or adjusted under 35 U.S.C. 154(b) by 0 days.

(21) Appl. No.: 14/353,069

(22) PCT Filed: Oct. 22, 2012

(86) PCT No.: PCT/US2012/061314

§ 371 (c)(1),
(2) Date: Apr. 21, 2014

(87) PCT Pub. No.: WO2013/059786

PCT Pub. Date: Apr. 25, 2013

(65) Prior Publication Data

US 2014/0294839 A1 Oct. 2, 2014

Related U.S. Application Data

(60) Provisional application No. 61/550,053, filed on Oct. 21, 2011.

(51) Int. Cl.

| | |
|---|---|
| ***A61K 39/00*** | (2006.01) |
| ***G01N 33/00*** | (2006.01) |
| ***C07K 16/18*** | (2006.01) |
| ***G01N 33/68*** | (2006.01) |
| ***C07K 14/435*** | (2006.01) |

(52) U.S. Cl.

CPC .......... *C07K 16/18* (2013.01); *A61K 39/0007* (2013.01); *C07K 14/435* (2013.01); *G01N 33/6848* (2013.01); *G01N 33/6896* (2013.01); *C07K 2317/30* (2013.01); *C07K 2317/34* (2013.01); *G01N 2800/2821* (2013.01)

(58) Field of Classification Search

None

See application file for complete search history.

(56) References Cited

U.S. PATENT DOCUMENTS

| | | | |
|---|---|---|---|
| 5,811,243 | A | 9/1998 | Strittmatter et al. |
| 2010/0316564 | A1 | 12/2010 | Sigurdsson |

OTHER PUBLICATIONS

Cuchillo-Ibanez 2008 "Phosphorylation of tau regulates its axonal transport by controlling its binding to kinesin" FASEB 22:3186-3195.*

Zhang 2011 "Long-term treatment with lithium alleviates memory deficits and reduces amyloid-.beta. producation in an aged alzheimer's disease transgenic mouse model" JAD 24(4):739-49 (abstract only).*

Liu 1991 "Abnormal tau proteins from Alzheimer's disease brains" JBC 266(32):21723-21727.*

Gilman 2005 "Clinical effects of a.beta. immunization an1792 in patients with AD in an interrupted trial" neurology 64:1553-1562.*

USCAFC 2014 "Myriad Genetics v Ambry Genetics".*

USCAFC 2015 "Ariosa Diagnostics v Sequenom".*

Cuchillo-Ibanez, I. et al., "Phosphylation of tau regulates its axonal transport by controling its binding to kinesin," FASEB J. (2008) 22:3186-3195.

Hoglinger, G.U. et al., "Microtubule-associated protein tau isoform 2 [*Homo sapiens*]," GenBank Accession No. NP_005901 [online], www.ncbi.nlm.nih.gov/protein/6754638?sat=14 &satkey=11322966 (Sep. 2011) 3 pgs.

International Search Report and Written Opinion in corresponding International Application No. PCT/US12/61314, mailed Feb. 25, 2013, 15 pgs.

Thomas, S. et al., "Dual modification of Alzheimer's disease PHF-tau protein by lysine methylation and ubiquitylation: a mass spectrometry approach," Acta. Neuropathol. (2011) 123:105-117.

Wischik, C.M. et al., "Isolation of a fragment of tau derived from the core of the paired helical filament of Alzheimer disease," Proc. Natl. Acad. Sci. (1998) 85:4506-4510.

Yamamoto, A. et al., "Deficiency in Protein L-Isoaspartyl Methyltransferase Results in a Fatal Progressive Epilepsy," J. Neurosci. (1988) 18(6):2063-2074.

* cited by examiner

*Primary Examiner* — Adam M Weidner

(74) *Attorney, Agent, or Firm* — Wood Herron & Evans LLP

(57) ABSTRACT

In sporadic Alzheimer's disease, neurofibrillary lesion formation is preceded by extensive post-translational modification of the microtubule associated protein tau. Immunoassays have been developed recently that detect tau in biological specimens, thus providing a means for pre-mortem diagnosis of Alzheimer's disease, which has remained elusive. These assays have been improved by the analysis of relevant post-translational modifications, such as phosphorylation, however opportunity for improvement remains. The present invention addresses this issue by disclosing synthetic methylated peptides derived from the tau protein of paired helical filaments and non-diseased control brain. Alzheimer's disease specificity is provided by the presence or absence of methyl moieties on lysine residues and differences between mono-, di-, and tri-methylation. The methylated peptide is useful as an antigen and a binding partner for identifying compounds that interact with the peptide and the methylated tau protein, including antibodies that can distinguish non-diseased brain from that affected by Alzheimer's disease. The resulting antibodies are useful diagnostically and therapeutically. The compounds that specifically bind to methylated tau proteins are useful for eliminating abnormally methylated tau.

4 Claims, 12 Drawing Sheets
(1 of 12 Drawing Sheet(s) Filed in Color)

```
  1  MAEPR(QEFEV) (MEDHAGTYGL) (GDRKDQGGYT) (MHQDQEGDTD) (AGLKESPLQT) (PTEDGSEEPG) [AD]
                                            [me2]                [me1]                  Normal
                                                                            [me1]
 61  (SETSDALSTP) (TAEDVTAPLV) (DEGAPGK)QAA  AQPHTEIPEG  TT[AEEAGIGD]       [TPSLEDEAAG]

121  HVTQARMVSK   SKDGTGSDDK   KAKGADGKTK    (IATPR)(GAAPP]  [GQK](GQANATR) (IPAKTPPAPK)
                                                   [me1]                    [me1] [me1]

181  TPPSSGEPPK   SGDRSGYSSP   GSPGTPGSR(S)                  (RTPSLPTPPT) (R)EPKK(VAVVR) (TPPKSPSSAK)
                                                                                 [me1]
                           [me1]                                   PHF6*
241  (SRLQTAPVPM) (PDLKNVKSKI) (GSTENLK)HQP  GGGK(VQIINK)   (KLDLSNVQSK)  CGSKDNIK(HV)
                         [me2]                                  [me2]
            PHF6
301  (PGGGSVQIVY) (KPVDLSK)VTS  KCGSLGNIHH   KPGGGQVEVK   SEKLDFK[DR](V) (QSKIGSLDNI)
                        [me2]                            [me2]                 [me2]

361  (THVPGGGNK)K  IETHKLTFRE   NAKAK(TDHGE) (EIVYKSPVVS) (GDTSPRHLSN)    (VSSTGSIDMV)
          [me2]

421  (DSPQLATLAD) (EVSASLAK)QG L
```

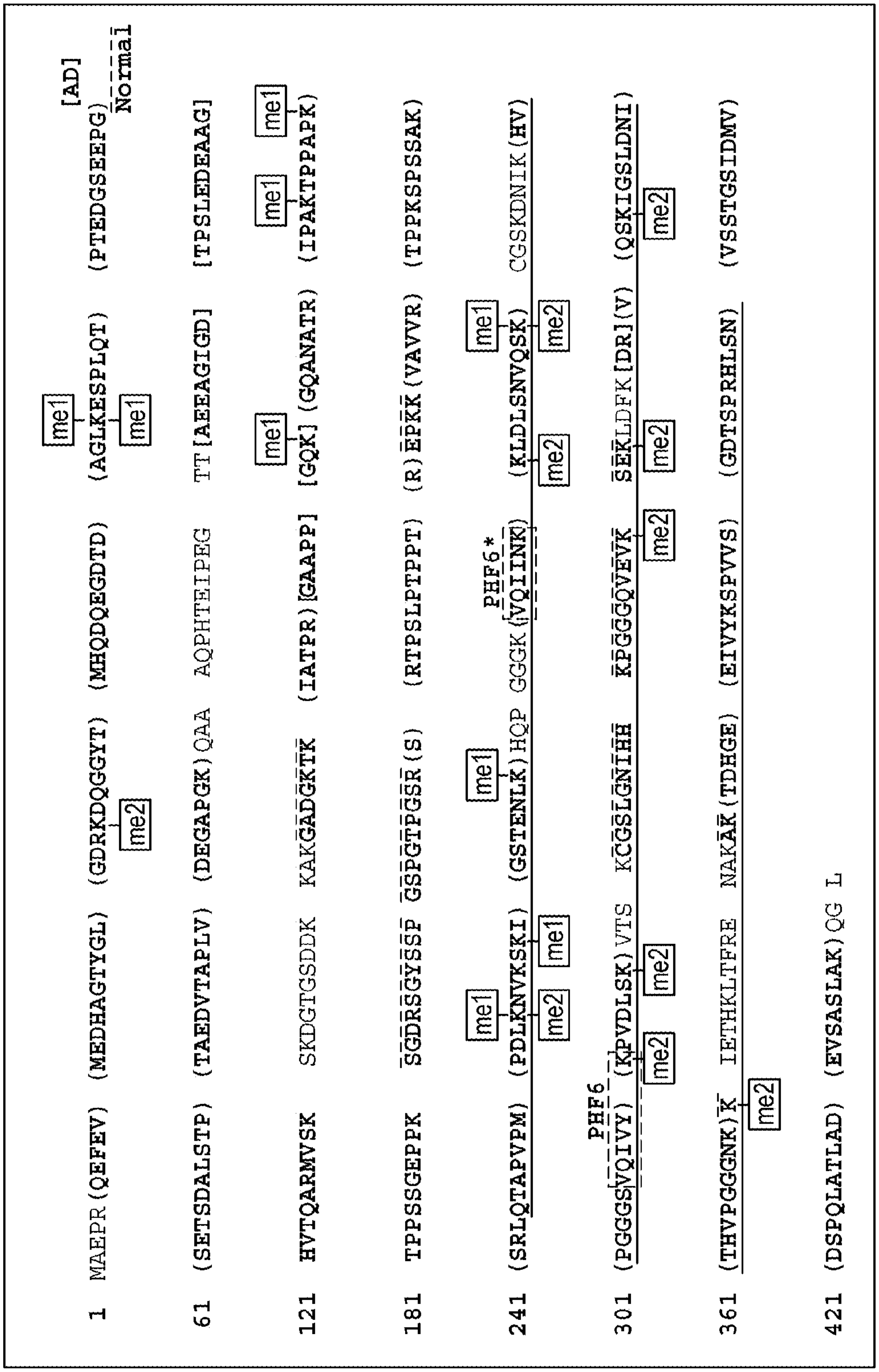

FIG. 1

```
  1  MAEPR[QEFEV] [MEDHAGTYGL] [GDRKDQGGYT] [MHQDQEGDTD] [AGLKESPLQT] [PTEDGSEEPG]
                                            me2                      me1
                                            ReMe

 61  [SETSDALSTP] [TAEDVTAPLV] [DEGAPGK]QAA AQPHTEIPEG              TTAEEAGTGD TPSLEDEAAG
                               ReMe

121  HVTQARMVSK   SKDGTGSDDK   KAK[GADGKTK] [IATPR]GAAPP            GQK[GQANATR] [IPAKTPPAPK]
                                                                      ReMe

181  [TPPSSGEPPK] [SGDRSGYSSP] [GSPGTPGSRS] [RTPSLPTPPT]             [REPKKVAVVR] [TPPKSPSSAK]
                                                                       ReMe         ReMe  ReMe

241  [SRLQTAPVPM] [PDLKNVKSKI] [GSTENLK]HQP GGGK[VQIINK]             [KLDLSNVQSK]  CGSKDNIK[HV]
                  me2                                                  me2
                  ReMe                                                 ReMe

301  [PGGGSVQIVY] [KPVDLSK]VTS K[CGSLGNIHH] [KPGGGQVEVK]             SEKLDFKDR[V]  [QSKIGSLDNI]
      me2          me2    U                                  U        me2            me2
      ReMe                                                                           ReMe

361  [THVPGGGNKK] IETHKLTFRE   NAK[AKTDHGE] [EIVYKSPVVS]             [GDTSPRHLSN]  [VSSTGSIDMV]
      me2                         ReMe       ReMe
      ReMe

421  [DSPQLATLAD] [EVSASLAK]QG L
```

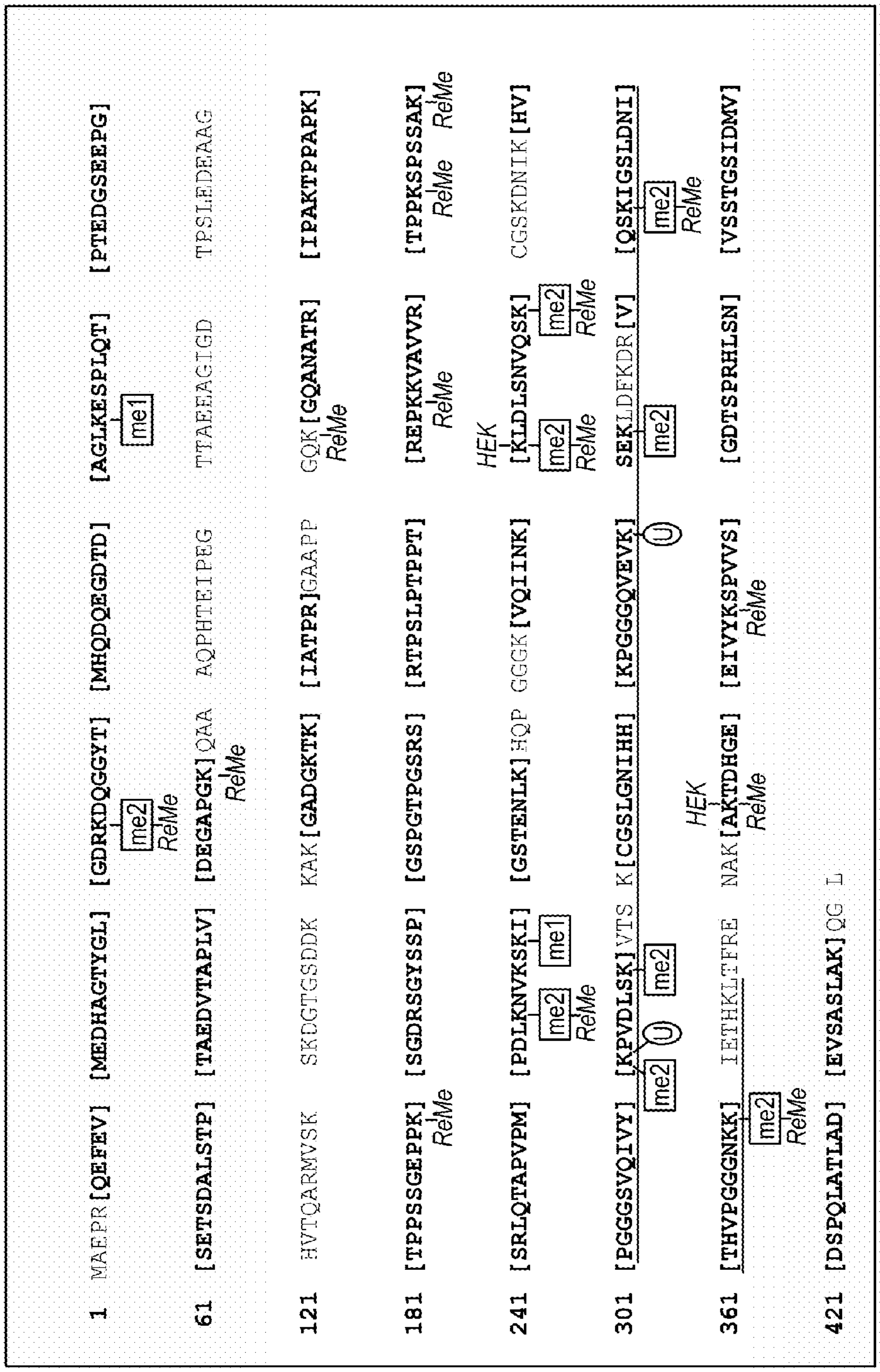

FIG. 6A

SEQUENCE LISTING

```
<160> NUMBER OF SEQ ID NOS: 17

<210> SEQ ID NO 1
<211> LENGTH: 12
<212> TYPE: PRT
<213> ORGANISM: Homo sapiens

<400> SEQUENCE: 1

Val Gln Ile Val Tyr Lys Pro Val Asp Leu Ser Lys
1               5                   10


<210> SEQ ID NO 2
<211> LENGTH: 20
<212> TYPE: PRT
<213> ORGANISM: Homo sapiens

<400> SEQUENCE: 2

Lys Asp Gln Gly Gly Tyr Thr Met His Gln Asp Gln Glu Asp Thr Asp
1               5                   10                  15

Ala Gly Leu Lys
            20


<210> SEQ ID NO 3
<211> LENGTH: 20
<212> TYPE: PRT
<213> ORGANISM: Homo sapiens

<400> SEQUENCE: 3

Asp Gln Gly Gly Tyr Thr Met His Gln Asp Gln Glu Gly Asp Thr Asp
1               5                   10                  15

Ala Gly Leu Lys
            20


<210> SEQ ID NO 4
<211> LENGTH: 15
<212> TYPE: PRT
<213> ORGANISM: Homo sapiens

<400> SEQUENCE: 4

Leu Gln Thr Ala Pro Val Pro Met Pro Asp Leu Lys Asn Val Lys
1               5                   10                  15
```

-continued

<210> SEQ ID NO 5
<211> LENGTH: 10
<212> TYPE: PRT
<213> ORGANISM: Homo sapiens

<400> SEQUENCE: 5

Ser Lys Ile Gly Ser Thr Glu Asn Leu Lys
1 5 10

<210> SEQ ID NO 6
<211> LENGTH: 10
<212> TYPE: PRT
<213> ORGANISM: Homo sapiens

<400> SEQUENCE: 6

Lys Leu Asp Leu Ser Asn Val Gln Ser Lys
1 5 10

<210> SEQ ID NO 7
<211> LENGTH: 10
<212> TYPE: PRT
<213> ORGANISM: Homo sapiens

<400> SEQUENCE: 7

Lys Leu Asp Leu Ser Asn Val Gln Ser Lys
1 5 10

<210> SEQ ID NO 8
<211> LENGTH: 12
<212> TYPE: PRT
<213> ORGANISM: Homo sapiens

<400> SEQUENCE: 8

Val Gln Ile Val Tyr Lys Pro Val Asp Leu Ser Lys
1 5 10

<210> SEQ ID NO 9
<211> LENGTH: 22
<212> TYPE: PRT
<213> ORGANISM: Homo sapiens

<400> SEQUENCE: 9

Cys Gly Ser Leu Gly Asn Ile His His Lys Pro Gly Gly Gly Gln Val
1 5 10 15

Glu Val Lys Ser Glu Lys
20

<210> SEQ ID NO 10
<211> LENGTH: 20
<212> TYPE: PRT
<213> ORGANISM: Homo sapiens

<400> SEQUENCE: 10

Val Gln Ser Lys Ile Gly Ser Leu Asp Asn Ile Thr His Val Pro Gly
1 5 10 15

Gly Gly Asn Lys
20

<210> SEQ ID NO 11
<211> LENGTH: 16
<212> TYPE: PRT
<213> ORGANISM: Homo sapiens

<400> SEQUENCE: 11

Ile Gly Ser Leu Asp Asn Ile Thr His Val Pro Gly Gly Gly Asn Lys
1 5 10 15

<210> SEQ ID NO 12
<211> LENGTH: 13
<212> TYPE: PRT
<213> ORGANISM: Homo sapiens

<400> SEQUENCE: 12

Ile Ala Thr Pro Arg Gly Ala Ala Pro Pro Gly Gln Lys
1 5 10

<210> SEQ ID NO 13
<211> LENGTH: 11
<212> TYPE: PRT
<213> ORGANISM: Homo sapiens

<400> SEQUENCE: 13

Gly Gln Ala Asn Ala Thr Arg Ile Pro Ala Lys
1 5 10

<210> SEQ ID NO 14
<211> LENGTH: 6
<212> TYPE: PRT
<213> ORGANISM: Homo sapiens

<400> SEQUENCE: 14

Thr Pro Pro Ala Pro Lys
1 5

<210> SEQ ID NO 15
<211> LENGTH: 14
<212> TYPE: PRT
<213> ORGANISM: Homo sapiens

<400> SEQUENCE: 15

Ser Arg Leu Gln Thr Ala Pro Val Pro Met Pro Asp Leu Lys
1 5 10

<210> SEQ ID NO 16
<211> LENGTH: 10
<212> TYPE: PRT
<213> ORGANISM: Homo sapiens

<400> SEQUENCE: 16

Ser Lys Ile Gly Ser Thr Glu Asn Leu Lys
1 5 10

<210> SEQ ID NO 17
<211> LENGTH: 19
<212> TYPE: PRT
<213> ORGANISM: Homo sapiens

<400> SEQUENCE: 17

His Val Pro Gly Gly Gly Ser Val Gln Ile Val Tyr Lys Pro Val Asp
1 5 10 15

Leu Ser Lys

METHYLATED PEPTIDES DERIVED FROM TAU PROTEIN AND THEIR ANTIBODIES FOR DIAGNOSIS AND THERAPY OF ALZHEIMER'S DISEASE

CROSS-REFERENCE TO RELATED APPLICATIONS

This application is a U.S. national phase filing under 35 U.S.C. 371 of International Patent Application No. PCT/US2012/061314, entitled "Methylated Peptides Derived from Tau Protein and their Antibodies for Diagnosis and Therapy of Alzheimer's Disease," filed on Oct. 22, 2012, which claims priority to and the benefit of the filing date of U.S. Patent Application No. 61/550,053, entitled "Methylated Peptides Derived from Tau Protein and their Antibodies for Diagnosis and Therapy of Alzheimer's Disease," filed on Oct. 21, 2011, the disclosures of which are incorporated by reference herein in their entireties.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Grant No. AG14452 awarded by the National Institutes of Health.

FIELD OF THE INVENTION

The present invention relates generally to immunogens, immunogenic compositions, and pharmaceutical compositions including peptides for the diagnosis or treatment of neurological disorders, such as Alzheimer's disease, and more specifically to such compositions including tau peptides.

BACKGROUND OF THE INVENTION

This section is intended to introduce the reader to various aspects of art that may be related to various aspects of the present invention, which are described and/or claimed below. This discussion is believed to be helpful in providing the reader with background information to facilitate a better understanding of various aspects of the present invention. Accordingly, it should be understood that these statements are to be read in this light, and not as admissions of prior art.

Tau proteins are proteins that stabilize microtubules. They are abundant in neurons in the central nervous system. When tau proteins are defective, and do not stabilize microtubules properly, they can result in tauopathies. Tauopathies are neurodegenerative diseases resulting from the pathological aggregation of tau protein in the human brain. The best known tauopathy is Alzheimer's disease ("AD"). Some other tauopathies include certain forms of frontotemporal lobar degeneration (e.g., Pick's disease, progressive supranuclear palsy, corticobasal degeneration, etc.) and chronic traumatic encephalopathy.

AD is the most common form of dementia, and is a terminal neurodegenerative disease that lasts about 8 years from diagnosis to death [Hebert L E, Scherr P A, Bienias J L, Bennett D A, Evans D A (2003) Alzheimer disease in the US population: prevalence estimates using the 2000 census. Arch Neurol 60:1119-1122; Thies W, Bleiler L (2011) 2011 Alzheimer's disease facts and figures. Alzheimers Dement 7:208-244]. It was first described by German psychiatrist and neuropathologist Alois Alzheimer in 1906 and was named after him. AD is a progressive neurodegenerative disorder primarily affecting brain regions associated with memory, judgment, and other higher cognitive functions. It is the leading cause of dementia in the world, with a current prevalence of over 5 million cases in the U.S. alone. Most often, it is diagnosed in people over 65 years of age, although the less-prevalent early-onset AD can occur much earlier. Owing to the aging population, this number is expected to triple in the coming decades. Thus, AD will continue to be a major source of morbidity and a driver of health care costs in the U.S. as it affects nearly one in three seniors>80 years of age.

Although the course of AD is unique for every individual, there are many common symptoms. The earliest observable symptoms are often mistakenly thought to be 'age-related' concerns, or manifestations of stress. In the early stages, the most common symptom is inability to acquire new memories, observed as difficulty in recalling recent events. When AD is suspected, the diagnosis is usually confirmed with behavioral assessments and cognitive tests, often followed by a brain scan.

As the disease advances, symptoms include confusion, irritability and aggression, mood swings, language breakdown, long-term memory loss, and the general withdrawal of the sufferer as their senses decline. Gradually, bodily functions are lost, ultimately leading to death. Individual prognosis is difficult to assess, as the duration of the disease varies. AD develops for an indeterminate period of time before becoming fully apparent, and it can progress undiagnosed for years.

Evidence gathered to date suggests that AD is primarily a sporadic disease, with genetic mutations accounting for only a small percentage of cases. As a result, identifying the causes of disease onset and progression in an aging but otherwise normal population remains among the highest priorities in biological science. Traditionally, the search for clues begins with disease pathology since AD is definitively diagnosed only upon autopsy. AD is characterized by the presence of two types of neuropathological hallmarks: neurofibrillary tangles (NFTs) and senile plaques. NFTs are intraneuronal aggregates of the microtubule associated protein tau. They are formed by hyperphosphorylation of tau protein, causing it to aggregate in an insoluble form. These aggregations of hyperphosphorylated tau protein may also be referred to as "paired helical filaments" (PHF). The precise mechanism of tangle formation is not completely understood, and whether tangles are a primary causative factor in the disease or play a more peripheral role is still a matter of debate. Senile plaques are extracellular and are primarily composed of amyloid β-peptide. The mechanism through which these lesions develop and the methods needed to detect them in living cases has remained obscure since their discovery more than 100 years ago.

The mechanisms that drive tau lesion formation in the highly prevalent sporadic form of AD are not fully understood, but appear to involve abnormal post-translational modifications (PTMs) that influence tau function, stability, and aggregation propensity. For example, hyperphosphorylation of tau protein on certain hydroxy-amino acids favors lesion formation by dissociating tau from its microtubule binding partner [Biernat J, Gustke N, Drewes G, Mandelkow E M, Mandelkow E (1993) Phosphorylation of Ser262 strongly reduces binding of tau to microtubules: distinction between PHF-like immunoreactivity and microtubule binding. Neuron 11:153-163; Bramblett G T, Goedert M, Jakes R, Merrick S E, Trojanowski J Q, Lee V M (1993)

Abnormal tau phosphorylation at Ser396 in Alzheimer's disease recapitulates development and contributes to reduced microtubule binding. Neuron 10:1089-1099] and by directly raising its rate and extent of aggregation [Alonso A, Zaidi T, Novak M, Grundke-Iqbal I, Iqbal K (2001) Hyperphosphorylation induces self-assembly of tau into tangles of paired helical filaments/straight filaments. Proc Natl Acad Sci USA 98:6923-6928, Esteve P O, Chang Y, Samaranayake M et al (2011) A methylation and phosphorylation switch between an adjacent lysine and serine determines human DNMT1 stability. Nat Struct Mol Biol 18:42-48; Necula M, Kuret J (2004) Pseudophosphorylation and glycation of tau protein enhance but do not trigger fibrillization in vitro. J Biol Chem 279:49694-49703]. Although tau phosphorylation state is mediated directly by phosphotransferases, it also is modulated by competing modifications on hydroxylamino acids such as O-linked β-N-acetylglucosaminylation (O-GlcNAcylation) [Liu F, Iqbal K, Grundke-Iqbal I, Hart G W, Gong C X (2004) O-GlcNAcylation regulates phosphorylation of tau: a mechanism involved in Alzheimer's disease. Proc Natl Acad Sci USA 101:10804-10809]. The reciprocal relationship between these tau modifications is leveraged by O-GlcNAcase inhibitors, which by increasing O-GlcNAcylation, lower phosphorylation stoichiometry and depress neurofibrillary lesion formation [Yuzwa S A, Vocadlo D J (2009) O-GlcNAc modification and the tauopathies: insights from chemical biology. Curr Alzheimer Res 6:451-454]. In addition to hydroxy amino acids, Lys residues are modified on tau protein, and these too can influence tau metabolism and aggregation. For example, ubiquitylation of tau at Lys residues modulates intracellular tau levels [Petrucelli L, Dickson D, Kehoe K et al (2004) CHIP and Hsp70 regulate tau ubiquitination, degradation and aggregation. Hum Mol Genet. 13:703-714, Shimura H, Schwartz D, Gygi S P, Kosik K S (2004) CHIP-Hsc70 complex ubiquitinates phosphorylated tau and enhances cell survival. J Biol Chem 279:4869-4876], the magnitude of which affects both nucleation and extension phases of the aggregation reaction [Congdon E E, Kim S, Bonchak J, Songrug T, Matzavinos A, Kuret J (2008) Nucleation-dependent tau filament formation: the importance of dimerization and an estimation of elementary rate constants. J Biol Chem 283:13806-13816]. Together these observations suggest that tau aggregation is under complex regulatory control that involves crosstalk among diverse and sometimes competing PTMs.

Presently, there are no easy, straightforward, noninvasive, definitive methods to diagnose Alzheimer's disease. Biopsy samples from a subject could be used to definitively diagnose AD, but risks include possible anesthetic complications, hemorrhage, infections or seizures [Schuette A J, Taub J S, Hadjipanayis C G, Olson J J (2010) Open biopsy in patients with acute progressive neurologic decline and absence of mass lesion. Neurology 75:419-424, Warren J D, Schott J M, Fox N C et al (2005) Brain biopsy in dementia. Brain 128:2016-2025]. For this reason, AD is currently determined in living subjects by review of medical history, administration of a panel of neuropsychiatric examinations, and structural CT and/or MRI imaging (to eliminate the possibility of vascular dementia, normal pressure hydrocephalus, subdural hematoma or solid tumor) [Knopman D S, DeKosky S T, Cummings J L et al (2001) Practice parameter: diagnosis of dementia (an evidence-based review). Report of the Quality Standards Subcommittee of the American Academy of Neurology. Neurology 56:1143-1153; McKhann G, Drachman D, Folstein M, Katzman R, Price D, Stadlan E M (1984) Clinical diagnosis of Alzheimer's disease: report of the NINCDS-ADRDA Work Group under the auspices of Department of Health and Human Services Task Force on Alzheimer's Disease. Neurology 34:939-944]. This method is at best 80% sensitive and 70% specific [Knopman D S, DeKosky S T, Cummings J L et al (2001) Practice parameter: diagnosis of dementia (an evidence-based review). Report of the Quality Standards Subcommittee of the American Academy of Neurology. Neurology 56:1143-1153]. AD currently is only definitively diagnosed at autopsy. However, NFTs appear long before death, and even decades before the onset of dementia [Braak H, Braak E (1991) Neuropathological stageing of Alzheimer-related changes. Acta Neuropathol 82:239-259], offering the opportunity to detect disease and intervene in disease progression at a much earlier stage than is possible today. Furthermore, because NFT load correlates with neurodegeneration [Gomez-Isla T, Price J L, McKeel D W, Jr., Morris J C, Growdon J H, Hyman B T (1996) Profound loss of layer II entorhinal cortex neurons occurs in very mild Alzheimer's disease. J Neurosci 16:4491-4500] and cognitive decline in AD [Ghoshal N, Garcia-Sierra F, Wuu J et al (2002) Tau conformational changes correspond to impairments of episodic memory in mild cognitive impairment and Alzheimer's disease. Exp Neurol 177:475-493], direct pre mortem detection could help monitor the effectiveness of drug treatments over time [Small G W, Bookheimer S Y, Thompson P M et al (2008) Current and future uses of neuroimaging for cognitively impaired patients. Lancet Neurol 7:161-172], while improving the performance and cutting the costs of clinical trials.

To capture changes in tau burden in living cases, powerful immunoassays, namely enzyme-linked immunosorbent assay (ELISA), capable of detecting minute quantities of tau analytes in cerebral spinal fluid (CSF) have been developed. However, the molecular characterization of tau in CSF presents an analytical challenge for several reasons. First, in the adult human brain there are six different tau isoforms produced from a single gene by alternative mRNA splicing. This heterogeneity is compounded by extensive post-translational modifications. Second, there is relatively low concentration of tau in CSF, ranging from approximately 300 ng/L in healthy individuals to approximately 900 ng/L in AD-afflicted individuals. Considering that this quantity is distributed over many differentially modified forms and six splice variants, the amount available for analysis of each molecular species falls close to the detection limit of most assays. Nevertheless, the first study in which total tau was successfully analyzed in CSF was published in 1995, demonstrating that total tau (t-tau) concentration was significantly elevated in AD patients compared to other neurodegenerative disorders [Arai H, Terajima M, Miura M et al (1995) Tau in cerebrospinal fluid: a potential diagnostic marker in Alzheimer's disease. Ann Neurol 38:649-652; Blennow K, Wallin A, Agren H, Spenger C, Siegfried J, Vanmechelen E (1995) Tau protein in cerebrospinal fluid: a biochemical marker for axonal degeneration in Alzheimer disease? Mol Chem Neuropathol 26:231-245].

Initial studies used antibodies insensitive to the modification status of the protein, thereby measuring the t-tau protein concentration. Of the more than 50 studies conducted on AD patients and controls to date, almost all have shown an increase in t-tau in AD patients by approximately 300% with a sensitivity and specificity of 80-90% [Blennow K, Hampel H (2003) CSF markers for incipient Alzheimer's disease. Lancet Neurol 2:605-613; Blennow K, Zetterberg H (2009) Cerebrospinal fluid biomarkers for Alzheimer's disease. J Alzheimers Dis 18:413-417; Hampel H, Burger K, Teipel S J, Bokde A L, Zetterberg H, Blennow K (2008) Core candidate neurochemical and imaging biomarkers of Alzheimer's disease. Alzheimers Dement 4:38-48; Shaw L M, Vanderstichele H, Knapik-Czajka M et al (2009) Cerebrospinal fluid biomarker signature in Alzheimer's disease neuroimaging initiative subjects. Ann Neurol 65:403-413]. However, t-tau has significantly greater discriminative power in the young (<70 years old) compared to the old (>70 years old) [Burger nee Buch K, Padberg F, Nolde T et al (1999) Cerebrospinal fluid tau protein shows a better discrimination in young old (<70 years) than in old old patients with Alzheimer's disease compared with controls. Neurosci Lett 277:21-24]. As some phosphorylated motifs (p-tau) are characteristic of AD, by using antibodies specific to such modifications, these assays have been greatly improved. For example p-tau231 and p-tau181 can be used to distinguish AD from control groups and even from other neurological conditions, including frontotemporal lobar degeneration, dementia with Lewy bodies, vascular dementia, and major depression [Bian H, Van Swieten J C, Leight S et al (2008) CSF biomarkers in frontotemporal lobar degeneration with known pathology. Neurology 70:1827-1835, Buerger K, Zinkowski R, Teipel S J et al (2003) Differentiation of geriatric major depression from Alzheimer's disease with CSF tau protein phosphorylated at threonine 231. Am J Psychiatry 160:376-379; Grossman M, Farmer J, Leight S et al (2005) Cerebrospinal fluid profile in frontotemporal dementia and Alzheimer's disease. Ann Neurol 57:721-729; Hampel H, Buerger K, Zinkowski R et al (2004) Measurement of phosphorylated tau epitopes in the differential diagnosis of Alzheimer disease: a comparative cerebrospinal fluid study. Arch Gen Psychiatry 61:95-102; Hampel H, Teipel S J (2004) Total and phosphorylated tau proteins: evaluation as core biomarker candidates in frontotemporal dementia. Dement Geriatr Cogn Disord 17:350-354; Vanmechelen E, Vanderstichele H, Davidsson P et al (2000) Quantification of tau phosphorylated at threonine 181 in human cerebrospinal fluid: a sandwich ELISA with a synthetic phosphopeptide for standardization. Neurosci Lett 285:49-52]. CSF p-tau levels correlate with cognitive decline in patients with mild cognitive impairment (MCI) [Buerger K, Teipel S J, Zinkowski R et al (2002) CSF tau protein phosphorylated at threonine 231 correlates with cognitive decline in MCI subjects. Neurology 59:627-629] and with neocortical NFT-pathology in AD [Buerger K, Ewers M, Pirttila T et al (2006) CSF phosphorylated tau protein correlates with neocortical neurofibrillary pathology in Alzheimer's disease. Brain 129:3035-3041]. Furthermore both t-tau and p-tau predict rate of cognitive decline in different stages of AD [Blom E S, Giedraitis V, Zetterberg H et al (2009) Rapid progression from mild cognitive impairment to Alzheimer's disease in subjects with elevated levels of tau in cerebrospinal fluid and the APOE epsilon4/epsilon4 genotype. Dement Geriatr Cogn Disord 27:458-464; Buerger K, Ewers M, Andreasen N et al (2005) Phosphorylated tau predicts rate of cognitive decline in MCI subjects: a comparative CSF study. Neurology 65:1502-1503; Samgard K, Zetterberg H, Blennow K, Hansson O, Minthon L, Londos E (2010) Cerebrospinal fluid total tau as a marker of Alzheimer's disease intensity. Int J Geriatr Psychiatry 25:403-410] and concentration of p-tau231 declined longitudinally from mild to moderate AD [Hampel H, Buerger K, Kohnken R et al (2001) Tracking of Alzheimer's disease progression with cerebrospinal fluid tau protein phosphorylated at threonine 231. Ann Neurol 49:545-546] and correlated significantly at baseline with rate of hippocampal atrophy in mild to moderate AD, acting as an indicator of structural disease progression [Hampel H, Burger K, Pruessner J C et al (2005) Correlation of cerebrospinal fluid levels of tau protein phosphorylated at threonine 231 with rates of hippocampal atrophy in Alzheimer disease. Arch Neurol 62:770-773]. In a recent European multi-center-study, CSF p-tau reliably predicted AD in subjects with MCI with high accuracy (80%) as a single biomarker in a relatively short but clinically relevant observation interval of 1.5 years [Ewers M, Buerger K, Teipel S J et al (2007) Multicenter assessment of CSF-phosphorylated tau for the prediction of conversion of MCI. Neurology 69:2205-2212]. Combination of this biomarker with t-tau and $A\beta_{42}$ can be used with optimized accuracy to detect incipient AD in subjects with MCI with positive and negative predictive values of >80% [Hansson O, Zetterberg H, Buchhave P, Londos E, Blennow K, Minthon L (2006) Association between CSF biomarkers and incipient Alzheimer's disease in patients with mild cognitive impairment: a follow-up study. Lancet Neurol 5:228-234; Herukka S K, Hallikainen M, Soininen H, Pirttila T (2005) CSF Abeta42 and tau or phosphorylated tau and prediction of progressive mild cognitive impairment. Neurology 64:1294-1297; Mattsson N, Zetterberg H, Hansson O et al (2009) CSF biomarkers and incipient Alzheimer disease in patients with mild cognitive impairment. JAMA 302:385-393; Zetterberg H, Wahlund L O, Blennow K (2003) Cerebrospinal fluid markers for prediction of Alzheimer's disease. Neurosci Lett 352:67-69], thus addition of unique epitopes specific to pathological tau may provide further accuracy and sensitivity to already established methods of diagnosis.

However, the understanding of the PTMs is not complete, and so accuracy of the current diagnostic tests could still be improved. Further, even though some diagnostic methods have been developed (with limited success), there is still no method for locating and removing abnormally modified tau from the body.

SUMMARY OF INVENTION

Certain exemplary aspects of the invention are set forth below. It should be understood that these aspects are presented merely to provide the reader with a brief summary of certain forms the invention might take and that these aspects are not intended to limit the scope of the invention. Indeed, the invention may encompass a variety of aspects that may not be explicitly set forth below.

The present invention overcomes the drawbacks described in the Background regarding current diagnosis and treatment of AD. It does so, in various aspects, by providing immunogens, immunogenic compositions, and/or pharmaceutical compositions including peptides for the diagnosis or treatment of neurological disorders, such as AD—such as compositions including tau peptides.

For example, embodiments of the present invention may include compositions having at least one antigenic tau peptide that is capable of inducing an immune response. In particular embodiments, the compositions result in antibody responses, leading to an antibody titer against the self-antigen tau in its methylated form. Such immunogens, immunogenic compositions and/or pharmaceutical compositions exhibit numerous desirable properties, such as the ability to induce an immune response, in particular antibody responses, with therapeutic effect against the induction and development of neurodegenerative diseases associated with methylated tau, such as AD. Thus, aspects of the present invention provide increased understanding of relevant post-translational modifications, their complex interactions, and how their changes affect the conformation of tau and its fragments, and use this information to design compounds that are able to bind abnormally modified tau and remove it once it is formed.

A specific embodiment of the present invention provides an immunogen including at least one tau peptide linked to an immunogenic carrier, where said antigenic tau peptide includes a methyl-tau epitope chosen from meK-24, meK-44, meK-163, meK-174, meK-180, meK-254, meK-259, meK-267, meK-281, meK-290, meK-311, meK-317, meK-340, meK-343, meK-353, meK-369, or meK-395 epitope. In other words, and as is known to those of ordinary skill in the art, the methylation occurs at a lysine residue (K) at the particular locations noted (e.g., K-24, K-44, K-163, etc.), corresponding to the full length tau isoform.

Another aspect of the present invention provides a method for generating one or more antibodies useful in the specific diagnosis or exclusion of Alzheimer's disease. The method involves at least the step of administering to a mammal a synthetic methylated tau peptide.

Another aspect of the present invention provides a method of treating a patient with Alzheimer's disease comprising the step of administering to the patient a reagent, such as an antibody generated by the method mentioned above.

A further aspect of the present invention provides a method of treating a patient with Alzheimer's disease comprising the step of administering to the patient a methylated peptide of the invention. Administration of such a methylated peptide generates anti-peptide antibodies that are able to eliminate methylated tau peptide.

A further aspect of the present invention provides for the use of a methylated peptide of the invention in designing and identifying compounds useful in the diagnosis and treatment of Alzheimer's disease.

A further aspect of the present invention provides a method of diagnosing Alzheimer's disease comprising the step of quantifying the amount of methylated tau in a biological specimen.

A further aspect of the present invention involves the provision of therapies based on the present inventors' determination that Lys methylation protects against pathological tau aggregation during normal aging, and that tau methylation modification enzymes may be tractable targets for disease modifying therapies focused on halting neurofibrillary lesion formation in AD.

A further aspect of the present invention provides a method for verifying the detection of a methylated tau peptide in selective reaction monitoring mass spectrometry. In this method, one chromatographically separates a body fluid sample. Next, selective reaction monitoring mass spectrometry analysis of the chromatographically separated sample is conducted, in order to monitor the variation in intensity of each of a plurality of fragment ion species formed from the methylated tau peptide. Following this analysis, an overlay score is computed. The overlay score may be calculated from a sum of overlay qualities, each overlay quality corresponding to a different one of the fragment ion species and being determined from the correlation between the intensity of the corresponding fragment ion species and the sum of intensities of the other fragment ion species at a particular timepoint in chromatographic time. Finally, one may then determine whether the methylated tau peptide has been detected based on the computed overlay score.

Other aspects of the present invention are described further in the following detailed description.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The accompanying drawings, which are incorporated in and constitute a part of this specification, illustrate embodiments of the invention and, together with the general description of the invention given above and the detailed description of the embodiments given below, serve to explain the principles of the present invention.

FIG. 1 is a sequence showing modification sites identified by LC-MS/MS on immunopurified PHF-tau and normal tau. The sequence shown is the 441-residue isoform of human tau with NCBI accession number NP_005901 (2N4R tau) with modifications to AD tau shown above the sequence and modifications to normal tau shown below the sequence. In the Figure, brackets designate PHF-tau sequence coverage; a dashed line above the sequence designates normal tau sequence coverage, and parentheses designate mutual sequence coverage. Further, dashed lines designate PHF6, PHF6* motifs, underlining designates a repeat region [as defined in [Gomez-Isla T, Price J L, McKeel D W, Jr., Morris J C, Growdon J H, Hyman B T (1996) Profound loss of layer II entorhinal cortex neurons occurs in very mild Alzheimer's disease. J Neurosci 16:4491-4500, incorporated by reference herein in its entirety]], "me1" denotes a monomethylated site and "me2" denotes a dimethylated site.

FIGS. 6A-6B show a summary of modification sites identified by LC-MS/MS on tau enriched from cognitively normal human brain. The sequence shown in FIG. 6A is that of human 2N4R tau (NCBI accession number NP_005901). Brackets designate tau sequence coverage; underline, MTBR (as defined by (Goedert et al., 1989)); U, ubiquitylated sites; me1, monomethylated sites; me2, dimethylated sites; ReMe, sites modified by reductive methylation at high methylation stoichiometry (22 mol/mol); HEK, sites modified in tau-expressing HEK293 cells; identified by MS analysis reported herein and in (Cripps et al., 2006; Thomas et al., 2012). FIG. 6B is a tau methylation and phosphorylation site distribution map. AD-derived tau contains covalently bound phosphate distributed across more than 30 sites clustered primarily on each side of tau microtubule binding region (open diamonds). In contrast, monomethylation (black diamonds) and dimethylation (open circles) sites are located primarily within the microtubule binding repeat region. Methylation sites directly overlap with ubiquitylation sites identified by MS (black circles).

FIG. 7A shows a time course of methylation determined in the presence of [$^{14}$C]-formaldehyde (n=3). FIG. 7B shows the effect of tau methylation on its ability to promote tubulin assembly. Tubulin assembly was initiated by raising reaction temperature to 37° C. and monitored by change in absorbance at 340 nm. Plot shows tubulin assembly in the presence of no tau (open circles), unmodified tau (black circles), and tau methylated to 5 mol/mol (circles with vertical lines), 10 mol/mol (circles with horizontal lines), 16 mol/mol (circles with angled lines rising from lower left to upper right), and 22 mol/mol (circles with angled lines rising from lower right to upper left) stoichiometries. Data points represent 3 separate trials±SD. FIG. 7C is a replot of data from Panel B, where each bar represents the extent of polymerization in absorbance units+/−SD. Only very high methylation stoichiometry (≥6 mol/mol) significantly depressed polymerization extent relative to unmodified 2N4R tau. No significant difference was found between no tau control and very high methylation stoichiometry (22 mol/mol). ###, $p<0.001$ relative to no tau; ***, $p<0.001$ relative to unmodified tau, as determined by Bonferonni post hoc analysis.

FIG. 9A: Unmodified (solid circle) or 5 mol/mol methylated tau (hollow circle) were incubated (18 h at 37° C.) at varying bulk concentrations in the presence of 100 μM Thiazine red inducer, then assayed for total filament length by electron microscopy. Results were then plotted against bulk protein concentration, where each data point represents the mean±SD of triplicate determinations and the solid lines represent best fit of the data points to linear regression. The abscissa intercept was obtained by extrapolation (dotted lines) and taken as the critical concentration ($K_{crit}$). FIG. 9B is a replot of data from FIG. 9A, where each bar represents the $K_{crit}$±propagated SEE. Methylation increased $K_{crit}$ nearly 3-fold relative to unmodified tau. *, $p<0.001$, as determined by z-test. FIG. 9C shows filaments prepared from unmodified (solid circle) and 5 mol/mol methylated tau (hollow circle) in the presence of Thiazine red were diluted below $K_{crit}$ in assembly buffer, and the resultant disaggregation was followed as a function of time by electron microscopy. Each data point represents total filament length per field±SD (n=3), whereas the solid line represents best fit of data points to an exponential decay function. The first-order decay constant $k_{app}$ was estimated from each regression and used in conjunction with filament length (shown in figure) and number at time t=0 to calculate dissociate rate constant $k_e$−. $k_e$+ was then obtained from Eq. 4. FIG. 9D is a replot of data from FIG. 9**C, where each bar represents the ratio of rate constants for filament extension ($k_e$+) and dissociation ($k_e$−) determined for 5 mol/mol methylated versus unmodified tau±propagated SEE. A ratio of 1, corresponding to no difference in rate, is marked by the dashed line. Methylation increased filament dissociation while decreasing filament extension. *, $p<0.05$; , $p<0.01$ as determined by z-test for comparison of methylated versus unmodified rate constants. FIG. 9E: Either unmodified (solid circle) or 5 mol/mol methylated tau (hollow circle) were incubated at constant supersaturation (i.e., 0.3 μM above $K_{crit}$) in the presence of Thiazine red inducer, then assayed for filament formation as a function of time. Each data point represents average filament lengths/field calculated from triplicate electron microscopy images±SD whereas normalized curve (solid lines) represents best fit of data to a three parameter Gompertz growth function (Necula and Kuret, 2004a). Values for lag time were estimated from these plots. FIG. 9F is a replot of lag times calculated from FIG. 9E, where each bar represents the lag time±propagated SEE. Methylation increased lag time relative to unmodified tau. *, $p<0.001$, as determined by z-test, consistent with depression of filament nucleation.

DETAILED DESCRIPTION OF THE INVENTION

Figure 2:
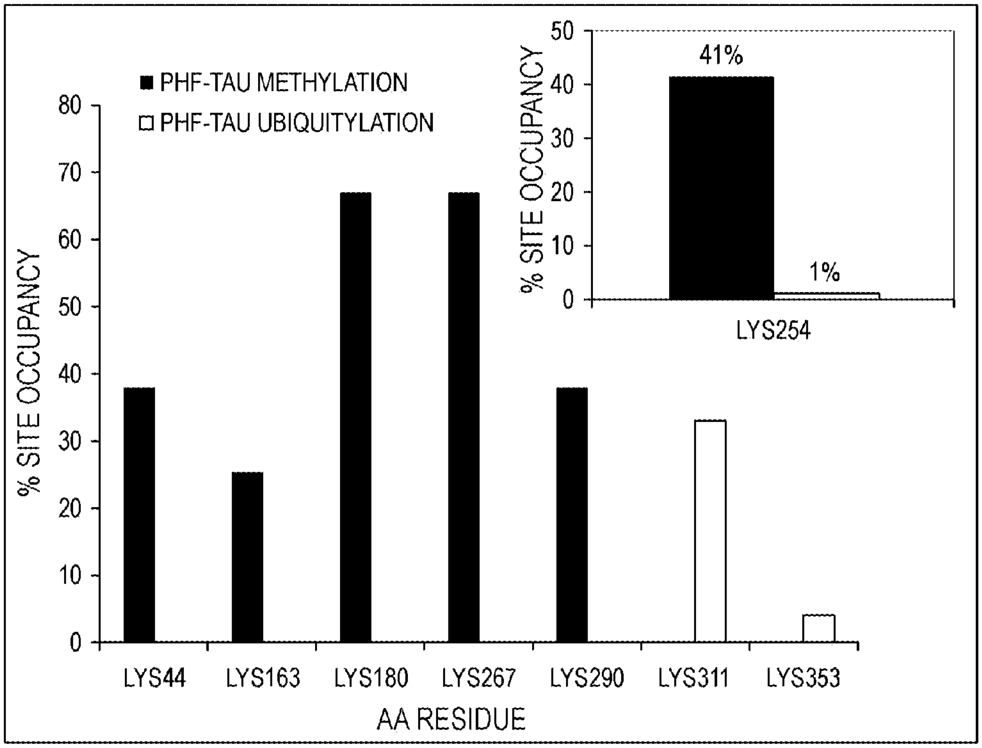
FIG. 2 is a chart showing the relative abundance of PHF-tau methylation and ubiquitylation at various lysine residues in the tau sequence. The relative abundance was calculated based on the spectral counts of the modified peptide/(modified peptide+unmodified peptide). Only sites having total spectral counts >3 are shown. The inset quantifies K254 methylation (41%) and ubiquitylation (1%). K254 was the most abundant methylated site identified on PHF-tau (spectral count=17) and the only site on PHF-tau identified in methylated and ubiquitylated forms.

One or more specific embodiments of the present invention will be described below. In an effort to provide a concise description of these embodiments, all features of an actual implementation may not be described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

As described above, the present invention overcomes the drawbacks described in the Background regarding current diagnosis and treatment of AD. It does so, in various aspects, by providing immunogens, immunogenic compositions, and/or pharmaceutical compositions including peptides, for the diagnosis or treatment of tauopathies, such as AD, certain forms of frontotemporal lobar degeneration, and chronic traumatic encephalopathy.

For example, embodiments of the present invention may include compositions having at least one antigenic tau peptide that is capable of inducing an immune response. In particular embodiments, the compositions result in antibody responses, leading to an antibody titer against the self-antigen tau in its methylated form. Such immunogens, immunogenic compositions and/or pharmaceutical compositions exhibit numerous desirable properties, such as the ability to induce an immune response, in particular antibody responses, with therapeutic effect against the induction and development of neurodegenerative diseases associated with methylated tau, such as AD. Thus, aspects of the present invention provide increased understanding of relevant post-translational modifications, their complex interactions, and how their changes affect the conformation of tau and its fragments, and use this information to design compounds that are able to bind abnormally modified tau and remove it once it is formed.

A specific embodiment of the present invention provides an immunogen including at least one tau peptide linked to an immunogenic carrier, where said antigenic tau peptide includes a methyl-tau epitope chosen from meK-24, meK-44, meK-163, meK-174, meK-180, meK-254, meK-259, meK-267, meK-281, meK-290, meK-311, meK-317, meK-340, meK-343, meK-353, meK-369, or meK-395 epitope. In other words, and as is known to those of ordinary skill in the art, the methylation occurs at a lysine residue (K) at the particular locations noted (e.g., 24, 44, 163, etc.) corresponding to full length 2N4R Tau.

Another aspect of the present invention provides a method for generating one or more antibodies useful in the specific diagnosis or exclusion of Alzheimer's disease. The method involves at least the step of administering to a mammal a synthetic methylated tau peptide.

Another aspect of the present invention provides a method of treating a patient with Alzheimer's disease comprising the step of administering to the patient a reagent, such as an antibody generated by the method mentioned above.

A further aspect of the present invention provides a method of treating a patient with Alzheimer's disease comprising the step of administering to the patient a methylated peptide of the invention. Administration of such a methylated peptide generates anti-peptide antibodies that are able to eliminate methylated tau peptide.

A further aspect of the present invention provides for the use of a methylated peptide of the invention in designing and identifying compounds useful in the diagnosis and treatment of Alzheimer's disease.

A further aspect of the present invention involves a structural analysis of tau aggregates isolated from authentic disease tissue specimens using mass spectrometry methods. The results revealed that a previously unrecognized tau modification, lysine methylation, copurified with tau aggregates. The methylation signature involved sites that are known to mediate tau ubiquitylation and other post-translational modifications, suggesting that methylation is a candidate modification for influencing tau aggregation and toxicity in disease. To extend the correlation between methylation occupancy and aggregation state, the modification state of soluble tau protein isolated from cognitively normal human brain was investigated, again using proteomic methods. Results showed that normal soluble tau was hypermethylated relative to AD-derived tau in its microtubule-binding repeat region. These data establish Lys methylation as normal tau post-translational modification in human brain. When purified recombinant human tau was subjected to Lys methylation in vitro, its tubulin assembly promoting activity was retained, but its aggregation propensity was greatly attenuated. Thus, another aspect of the present invention proposes that Lys methylation protects against pathological tau aggregation during normal aging, and that tau methylation modification enzymes may be tractable targets for disease modifying therapies focused on halting neurofibrillary lesion formation in AD.

A further aspect of the present invention involves the provision of therapies based on the present inventors' determination that Lys methylation protects against pathological tau aggregation during normal aging, and that tau methylation modification enzymes may be tractable targets for disease modifying therapies focused on halting neurofibrillary lesion formation in AD.

A further aspect of the present invention provides a method for verifying the detection of a methylated tau peptide in selective reaction monitoring mass spectrometry. In this method, one chromatographically separates a body fluid sample. Next, selective reaction monitoring mass spectrometry analysis of the chromatographically separated sample is conducted, in order to monitor the variation in intensity of each of a plurality of fragment ion species formed from the methylated tau peptide. Following this analysis, an overlay score is computed. The overlay score may be calculated from a sum of overlay qualities, each overlay quality corresponding to a different one of the fragment ion species and being determined from the correlation between the intensity of the corresponding fragment ion species and the sum of intensities of the other fragment ion species at a particular timepoint in chromatographic time. Finally, one may then determine whether the methylated tau peptide has been detected based on the computed overlay score. This method may further include assigning an elution time to the substance of interest (i.e., a methylated tau peptide), wherein the assigned elution time is a time along the chromatographic time scale for which the computed overlay score exceeds a predetermined threshold value. The assigned elution time may be a time along the chromatographic time scale for which the computed overlay score is a maximum value. The overlay score may be determined from an average of the overlay qualities.

Another specific embodiment of the present invention provides for the use of methylated tau protein as a biomarker for Alzheimer's disease, or predisposition thereto. Where said biomarker includes one or more of the following methylated residues: meK-24, meK-44, meK-163, meK-174, meK-180, meK-254, meK-259, meK-267, meK-281, meK-290, meK-311, meK-317, meK-340, meK-343, meK-353, meK-369, or meK-395, corresponding to the full length 2N4R tau protein.

More specifically, one aspect of the present invention provides methylated peptides useful in generating antibodies specific for the tau protein found in the brains of either non-diseased humans or those with AD. As described above in the Background, the mechanisms that drive tau lesion formation appear to involve abnormal post-translational modifications (PTMs) that influence tau function, stability, and aggregation propensity. First, for example, hyperphosphorylation of tau protein on certain hydroxy-amino acids favors lesion formation by dissociating tau from its microtubule binding partner [Biernat J, Gustke N, Drewes G, Mandelkow E M, Mandelkow E (1993) Phosphorylation of Ser262 strongly reduces binding of tau to microtubules: distinction between PHF-like immunoreactivity and microtubule binding. Neuron 11:153-163; Bramblett G T, Goedert M, Jakes R, Merrick S E, Trojanowski J Q, Lee V M (1993) Abnormal tau phosphorylation at Ser396 in Alzheimer's disease recapitulates development and contributes to reduced microtubule binding. Neuron 10:1089-1099, incorporated by reference herein in their entireties] and by directly raising its rate and extent of aggregation [Alonso A, Zaidi T, Novak M, Grundke-Iqbal I, Iqbal K (2001) Hyperphosphorylation induces self-assembly of tau into tangles of paired helical filaments/straight filaments. Proc Natl Acad Sci USA 98:6923-6928; Esteve P O, Chang Y, Samaranayake M et al (2011) A methylation and phosphorylation switch between an adjacent lysine and serine determines human DNMT1 stability. Nat Struct Mol Biol 18:42-48; Necula M, Kuret J (2004) Pseudophosphorylation and glycation of tau protein enhance but do not trigger fibrillization in vitro. J Biol Chem 279:49694-49703, incorporated by reference herein in their entireties]. Second, tau phosphorylation state also is modulated by competing modifications on hydroxylamino acids such as O-linked β-N-acetylglucosaminylation (O-GlcNAcylation) [Liu F, Iqbal K, Grundke-Iqbal I, Hart G W, Gong C X (2004) O-GlcNAcylation regulates phosphorylation of tau: a mechanism involved in Alzheimer's disease. Proc Natl Acad Sci USA 101:10804-10809, incorporated by reference herein in its entirety]. And third, in addition to hydroxy amino acids, Lys residues are modified on tau protein, and these too can influence tau metabolism and aggregation, [for example, ubiquitylation of tau at Lys residues modulates intracellular tau levels [Petrucelli L, Dickson D, Kehoe K et al (2004) CHIP and Hsp70 regulate tau ubiquitination, degradation and aggregation. Hum Mol Genet. 13:703-714; Shimura H, Schwartz D, Gygi S P, Kosik K S (2004) CHIP-Hsc70 complex ubiquitinates phosphorylated tau and enhances cell survival. J Biol Chem 279:4869-4876, incorporated by reference herein in their entireties], the magnitude of which affects both nucleation and extension phases of the aggregation reaction [Congdon E E, Kim S, Bonchak J, Songrug T, Matzavinos A, Kuret J (2008) Nucleation-dependent tau filament formation: the importance of dimerization and an estimation of elementary rate constants. J Biol Chem 283: 13806-13816]].

Thus, specificity for AD may be generated by the presence or absence of methyl moieties on the tau protein. And so, the methylated peptides of one aspect of the present invention, and the antibodies generated thereby in another aspect of the present invention, are useful diagnostically and/or therapeutically, as well as for drug design for AD.

The methylated peptides of this aspect of the present invention may be derived from the fragment of the tau protein present in the brains of either Alzheimer's patients or non-diseased humans. The tau protein may be obtained from a variety of sources, including adult-autopsy tissue, fetal sources, or biopsy-derived tissue, or may be synthesized using techniques known to those of skill in the art. All references to tau amino acid residues herein follow the numbering scheme according to the human tau isoform with NCBI accession number NP_005901 (shown in FIG. 1).

The tau protein fragment that may serve as a template for constructing the peptides of the invention may be between about 4 and about 20 amino acids in length, and more particularly between about 15 to about 20 amino acids in length. One of ordinary skill in the art can readily select appropriate fragments given the guidance provided herein coupled with the general knowledge of those of ordinary skill in the art. The tau protein fragment may be modified to contain, or synthesized to contain, at least one methylated amino acid. In a particular embodiment, the at least one amino acid is lysine.

Production/Synthetic Peptides

In certain embodiments, the tau protein fragments and the methylated peptides may be produced using synthetic techniques. For example, the peptides may be generated using a commercially available automatic synthesizer according to standard procedures well known to those of ordinary skill in the art. In this manner, methyl-lysine residues may be incorporated in the course of synthesis. Alternatively, other standard techniques known to those of ordinary skill in the art may be used (e.g., those disclosed in Huse W D, Sastry L, Iverson S A et al (1989) Generation of a Large Combinatorial Library of the Immunoglobulin Repertoire in Phage-Lambda. Science 246:1275-1281, incorporated by reference herein in its entirety).

Further, in view of the size of the tau peptide fragments and the methylated peptides of the various aspects of the present invention, these fragments and peptides may be prepared by recombinant DNA techniques (known to those of ordinary skill in the art) by cloning and expressing within a host microorganism or other cell, a DNA fragment carrying a coding sequence for a methylated peptide, antibody, or antibody fragment of the invention. The expression system may be chosen from those which are capable of adding the required number of methyl groups. Coding sequences for the peptides or antibodies of the invention can be prepared synthetically or can be derived from viral RNA by known techniques, or from available cDNA-containing plasmids (such techniques are well known to those of ordinary skill in the art). Thus, another aspect of the present invention encompasses nucleic acid sequences encoding the peptides, antibodies, or antibody fragments of the invention. These nucleic acid sequences are useful not only for recombinant production methods, but may be used in the diagnostic and therapeutic methods described herein.

Systems for cloning and expressing the methylated peptides of the invention in various cells, including, for example, bacterial, mammalian, yeast and insect cells, and suitable vectors may be readily selected from among known and available for private and public laboratories and depositories and from commercial vendors. The selection of suitable host cells and methods of transformation, culture, amplification, screening and product production and purification can be performed by one of skill in the art by reference to known techniques (such as those described in Ikonomovic M D, Abrahamson E E, Isanski B A et al (2006) X-34 labeling of abnormal protein aggregates during the progression of Alzheimer's disease. Methods Enzymol 412: 123-144, the disclosure of which is incorporated by reference herein in its entirety). The antibodies of the invention and fragments thereof are also amenable to recombinant production techniques, such as those described herein. Other systems that can be used include bacuolovirus and bacterial expression systems and vectors.

When produced by conventional recombinant means, the methylated peptides of the invention may be isolated either from the cellular contents by conventional lysis techniques or from cell medium by conventional methods, such as chromatography (such as those described in Iliev A I, Ganesan S, Bunt G, Wouters F S (2006) Removal of pattern-breaking sequences in microtubule binding repeats produces instantaneous tau aggregation and toxicity. J Biol Chem 281:37195-37204, the disclosure of which is incorporated by reference herein in its entirety).

Production of Antibodies/Inhibitors

The methylated peptides may be used for generating both polyclonal and monoclonal antibodies, or for testing the binding of other bivalent compounds. Specific antisera (polyclonal antibodies) may be generated using known techniques (such as those described in they AI, Ganesan S, Bunt G, Wouters F S (2006) Removal of pattern-breaking sequences in microtubule binding repeats produces instantaneous tau aggregation and toxicity. J Biol Chem 281: 37195-37204, the disclosure of which is incorporated by reference herein in its entirety). Similarly, monoclonal antibodies of the invention may be produced by conventional methods, including the Kohler and Milstein hybridoma technique, recombinant techniques [Huse W D, Sastry L, Iverson S A et al (1989) Generation of a Large Combinatorial Library of the Immunoglobulin Repertoire in Phage-Lambda. Science 246:1275-1281, incorporated by reference herein in its entirety], or any other techniques known to the art. These antibodies are specific for the methylated peptides from which they are generated, i.e., the antibodies do not bind unmodified tau fragments nor non-tau methylated fragments.

Aspects of the present invention further encompass functional fragments of the antibodies of the invention, including Fab, $F_v$, and $F(ab')_2$ fragments, synthetic molecules containing the binding site of the antibodies of the invention, and complementarity determining regions (CDRs) thereof. Further, these functional fragments may be used in the production of recombinant antibodies, including bifunctional antibodies, chimeric antibodies, and humanized antibodies, which preferably retain the antigen binding specificity of the antibodies of the invention, as produced according to known techniques (such as those described in Josephs K A, Whitwell J L, Ahmed Z et al (2008) Beta-amyloid burden is not associated with rates of brain atrophy. Ann Neurol 63:204-212, the disclosure of which is incorporated by reference herein in its entirety). These functional fragments and recombinant antibodies may be used for a variety of purposes, including any of those described herein for the antibodies of the invention.

In general, polyclonal antisera, monoclonal antibodies, and other antibodies that bind to a methylated peptide as the antigen (Ab1) are useful to identify epitopes of tau, to separate tau from contaminants in living tissue (e.g., in chromatographic columns and the like), and in general as research tools and for the production of other types of antibodies described above. Anti-idiotype antibodies (Ab2) are useful for binding tau and thus may be used in the treatment of AD. Other uses as research tools and as components for separation of tau from other contaminants of living tissue, for example, are also contemplated for these antibodies.

Diagnostic Applications

The present invention provides reagents and methods useful in detecting and diagnosing AD. Thus, the methylated peptides and antibodies of the aspects of the invention described above may be useful as diagnostic reagents. These reagents may optionally be labeled using diagnostic labels, such as radioactive labels, colorimetric enzyme label systems, and the like conventionally used in diagnostic or therapeutic models (as is known to those of ordinary skill in the art). Alternatively, the N- or C-terminus of a methylated peptide of the invention may be tagged with a detectable label that can be recognized by a specific antisera or another binding mechanism, e.g., biotin-streptavidin (as is known to those of ordinary skill in the art). The terminal labels include those detected by fluorometric, colormetric, etc., methods. The reagents may be used in diagnosis of Alzheimer's disease. For example, ELISA or other immunological methods can be used for the detection of methylated tau protein in cerebrospinal fluid (CSF) or blood; these methods make use of antibodies of the invention. The selection of the appropriate assay format and label system is within the skill of the art and may readily be selected by a skilled artisan.

As a result, methods for the detection of Alzheimer's disease are provided. The methods involve contacting a selected mammalian tissue, particularly human brain tissue, CSF, or serum, in a selected assay format based on the binding or hybridization of the reagent to the sample. Such assay formats are well known to those of ordinary skill in the art.

Therapeutic Applications

Compositions and methods useful for the treatment of conditions associated with Alzheimer's disease are also provided. The therapeutic compositions of the invention may be formulated to contain a methylated peptide or antibody of the invention, or a fragment thereof. In one embodiment, an antibody of the invention may be used for passive immunotherapy, which uses antibodies designed to attack foreign substances directly, while not stimulating the subject's immune system. For example, one type can use monoclonal antibodies generated as a targeted therapy (e.g., when the mAb cells binds to target, they help to kill them off, either through toxins, which have been attached to them in the lab, or through other means). In another embodiment, the methylated peptide is used as an immunogen for active immunotherapy, which aids and/or stimulates the subject's immune system to take an active role in attack. In still another embodiment, a compound (e.g., a bivalent reagent described below) identified through use of the methylated peptide of the invention is used for treatment of Alzheimer's disease.

The therapeutic composition may contain 0.01 μg to 10 mg peptide, protein, or reagent. These compositions may also include a pharmaceutically acceptable carrier. Suitable carriers are well known to those of skill in the art and include, for example, saline. Alternatively such compositions may include conventional delivery systems into which protein of the invention is incorporated. Optionally, these compositions may contain other active ingredients, e.g., chemotherapeutics. The dose, timing, and mode of administration of these compositions may be determined by one of skill in the art by well known methods. Such factors as age and condition of the patient may indicate increasing or decreasing the dose, frequency, or mode of administration of the therapeutic compositions of the invention. Generally, administration in a site-directed manner and is repeated as needed. Such therapy may be administered in conjunction with conventional therapies.

Drug Design

The methylated peptides of the present invention may also be used in the design, screening and development of simple chemical compounds, proteins, or complex biopolymers that have utility as diagnostic and/or therapeutic drugs for Alzheimer's disease.

As one example, a compound capable of bivalent binding to the methylated peptide or to methylated tau protein of the invention and either preventing or enhancing its biological activity may be a useful drug component for the treatment or prevention of Alzheimer's disease. Such a compound may be obtained using known techniques from a peptide library, an organic chemical library, or derived from a variety of sources, including, for example, extracts of supernatants from culture of bioorganisms, extracts from organisms collected from natural sources, known chemical compounds, and mixtures thereof.

Utilizing the methylated peptides or antibodies of the invention, conventional assays and techniques may be utilized for the screening and development of drugs capable of competitively binding to these peptides and proteins. An example of one suitable method involves the incubation of a test compound and the methylated peptide or an antibody of the invention that may be immobilized on a solid support. Alternatively, the incubation may be performed fully in solution (e.g., fluorescence polarization). Still other conventional methods of drug screening involve employing a suitable computer program to determine compounds having similar or complementary chemical structure to that of a methylated peptide or antibody of the invention and screening those compounds for competitive binding. Such methods are well known to those of ordinary skill in the art. However, it should be understood that one of skill in the art may readily select the type of conventional screening method most desirable, as well as the reagent of this invention, e.g., methylated peptide, antibody or fragment thereof.

Thus, through use of such methods, the present invention is anticipated to provide compounds capable of interacting with the methylated peptides of the invention, and either enhancing or decreasing its biological activity, as desired. Such designed drugs, or drugs identified through these screening assays, are specific for Alzheimer's disease and do not interact with normal proteins, including normal tau. Such specificity can be assessed using techniques known to those of ordinary skill in the art. For example, specificity of binding can be determined by comparing the binding of the identified compound (e.g., an inhibitor) to a methylated peptide of the invention and to an unmethylated or alternatively methylated version of the same amino acid stretch.

The present disclosure is further illustrated by the following Examples, which should not be construed as further limiting. The contents of all figures and all references, patents, and published patent applications cited throughout this disclosure are expressly incorporated herein by reference to their entirety.

EXAMPLES

Example 1

The following Example describes a study that determines the tau PTM signature(s) associated with neurofibrillary lesion formation. As will be apparent to those of ordinary skill in the art, the knowledge of such signature(s) provides for the isolation and/or development of tau peptides or peptide fragments or production of synthetic peptides or peptide fragments that can be used to achieve all of the various aspects of the present invention described above.

Background

To gain insight into the tau PTM signature most closely associated with neurofibrillary lesion formation at single amino acid resolution, mapping of modifications on authentic, paired helical filaments (PHFs) isolated from AD brain was performed using mass spectrometry methods, with special emphasis on Lys modifications [Cripps D, Thomas S N, Jeng Y, Yang F, Davies P, Yang A J (2006) Alzheimer disease-specific conformation of hyperphosphorylated paired helical filament-Tau is polyubiquitinated through Lys-48, Lys-11, and Lys-6 ubiquitin conjugation. J Biol Chem 281:10825-10838, incorporated by reference herein in its entirety]. Preliminary analysis identified K254, K311, and K353 within the tau microtubule binding repeat region as ubiquitylation sites that were at least partially occupied in PHFs [Cripps D, Thomas S N, Jeng Y, Yang F, Davies P, Yang A J (2006) Alzheimer disease-specific conformation of hyperphosphorylated paired helical filament-Tau is polyubiquitinated through Lys-48, Lys-11, and Lys-6 ubiquitin conjugation. J Biol Chem 281:10825-10838, incorporated by reference herein in its entirety]. Recently, acetylation was discovered as an early-stage Lys-directed in vivo tau modification associated with tau-bearing lesions in AD and frontotemporal lobar degeneration [Cohen T J, Guo J L, Hurtado D E et al (2011) The acetylation of tau inhibits its function and promotes pathological tau aggregation. Nat Commun 2:252; Min S W, Cho S H, Zhou Y et al (2011) Acetylation of tau inhibits its degradation and contributes to tauopathy. Neuron 67:953-966, incorporated by reference herein in their entireties]. Tau acetylated in vitro resulted in occupation of diverse sites that overlapped with those we had determined to be ubiquitylated in disease [Min S W, Cho S H, Zhou Y et al (2011) Acetylation of tau inhibits its degradation and contributes to tauopathy. Neuron 67:953-966, incorporated by reference herein in its entirety]. Therefore acetylation is another candidate modification for regulating tau turnover indirectly through the ubiquitin-proteasome system [Min S W, Cho S H, Zhou Y et al (2011) Acetylation of tau inhibits its degradation and contributes to tauopathy. Neuron 67:953-966, incorporated by reference herein in its entirety]. Moreover, in other biochemical pathways, such as histone-mediated control of gene expression, certain acetylated Lys residues can alternatively be methylated, contributing to complex cross-talk among Lys and hydroxyl-amino acid modifications [Latham J A, Dent S Y (2007) Cross-regulation of histone modifications. Nat Struct Mol Biol 14:1017-1024, incorporated by reference herein in its entirety]. These observations suggest that the web of tau PTMs is potentially complex, with Lys-directed modifications playing key regulatory roles with respect to rates of tau turnover and aggregation.

In this Example, characterization of both PHF-tau and pathologically normal tau is extended by using mass spectrometry methods and expanding search criteria to include both acetyl- and methyl-Lys modifications. The results show that Lys methylation is a widespread tau modification that changes with the onset of pathogenicity in vivo.

Materials and Methods

Antibodies—

Anti-tau mouse monoclonal antibodies Tau5 [LoPresti P, Szuchet S, Papasozomenos S C, Zinkowski R P, Binder L I (1995) Functional implications for the microtubule-associated protein tau: localization in oligodendrocytes. Proc Natl Acad Sci USA 92:10369-10373, incorporated by reference herein in its entirety] and AT8 [Goedert M, Jakes R, Vanmechelen E (1995) Monoclonal antibody AT8 recognises tau protein phosphorylated at both serine 202 and threonine 205. Neurosci Lett 189:167-169, incorporated by reference herein in its entirety] were obtained from Dr. L. I. Binder (Northwestern University Medical School, Chicago, Ill.) and Endogen (Woburn, Mass.), respectively. Rabbit polyclonal anti-meK antibody was obtained from Enzo Life Sciences (ADI-KAP-TF121; Plymouth Meeting, Pa.). Cy3-conjugated goat anti-rabbit IgG and Alexa Fluor 488-conjugated goat anti-mouse secondary antibodies were from Jackson Immuno Research Laboratories, Inc (West Grove, Pa.) and Invitrogen (Carlsbad, Calif.), respectively. Horseradish peroxidase-conjugated goat anti-rabbit IgG secondary antibody used for Western Blot was from Kirkegaard and Perry Laboratories Inc (Gaithersburg, Md.).

Subjects and Tissue Preparation—

This study used only archival, de-identified post mortem brain tissue samples from autopsies performed with informed consent of each patient or relative via procedures approved by the relevant institutional committees (University of Rochester, N.Y.). Paraformaldehyde-fixed brain tissue was obtained from three elderly subjects with a clinical diagnosis of AD (mean age 76±13 yrs (SD)) that was confirmed on neuropathological evaluation in which the Consortium to Establish a Registry for AD (CERAD) age-adjusted criteria were met [Mirra S S, Heyman A, McKeel D et al (1991) The Consortium to Establish a Registry for Alzheimer's Disease (CERAD); Part II. Standardization of the neuropathologic assessment of Alzheimer's disease. Neurology 41:479-486, incorporated by reference herein in its entirety]. All cases satisfied criteria for Braak stages V or VI [10]. As is known to those of ordinary skill in the art, the degree of NFT involvement in AD is defined by Braak stages. Braak stages I and II are used when NFT involvement is confined mainly to the transentorhinal region of the brain, stages III and IV when limbic regions such as the hippocampus are involved, and stages V and VI when there is extensive neocortical involvement.

Affinity Purification of PHF-Tau and Enzymatic Digestion—

PHF-tau was isolated from AD brain by immunoaffinity chromatography (MC1 monoclonal antibody) as previously described [Jicha G A, Bowser R, Kazam I G, Davies P (1997) Alz-50 and MC-1, a new monoclonal antibody raised to paired helical filaments, recognize conformational epitopes on recombinant tau. J Neurosci Res 48:128-132, incorporated by reference herein in its entirety]. PHF-tau was digested in solution in the presence of 40% methanol with either trypsin (Promega) or Lys-C (Sigma) followed by phosphopeptide enrichment (Immobilized gallium, Thermo Fisher Scientific) as detailed earlier [Cripps D, Thomas S N, Jeng Y, Yang F, Davies P, Yang A J (2006) Alzheimer disease-specific conformation of hyperphosphorylated paired helical filament-Tau is polyubiquitinated through Lys-48, Lys-11, and Lys-6 ubiquitin conjugation. J Biol Chem 281:10825-10838, incorporated by reference herein in its entirety].

Preparation of Tau from Human Control Brain—

The purification procedure was based on that of Ksiezak-Reding et al [Ksiezak-Reding H, Liu W K, Yen S H (1992) Phosphate analysis and dephosphorylation of modified tau associated with paired helical filaments. Brain Res 597:209-219, incorporated by reference herein in its entirety]. Briefly, brain tissue obtained at autopsy, which lacked neuropathology, was homogenized in 5 volumes of homogenization buffer (20 mM 2-(N-morpholino)ethanesulfonic acid (MES)/NaOH, pH 6.8, 80 mM NaCl, 1 mM $MgCl_2$, 2 mM EGTA, 0.1 mM EDTA, 1 mM PMSF, 10 mM sodium pyrophosphate, 20 mM NaF). The homogenate was separated by centrifugation (20 min at 27,000×g). The supernatant was subjected to heat treatment (10 min boiling) in the presence of 0.5 M NaCl and 2% 2-mercaptoethanol. After the heat treatment, the supernatant was collected (20 min at 27,000×g) and treated with 2.5% (final concentration) of perchloric acid (PCA) to remove acid-insoluble non-tau material. After centrifugation, the PCA-soluble extract was treated with trichloroacetic acid (TCA) up to 20% (w/v) and the TCA-precipitated proteins were collected. The TCA pellets were suspended in a buffer suitable for analysis.

Reductive Methylation of Recombinant Human 4R Tau—

Lyophilized recombinant full-length human 2N4R tau (100 μg) was re-suspended in 0.1M citrate buffer (pH 6) and methylated (room temperature for 2 h) in the presence of 0.1 M sodium cyanoborohydride and 20 mM formaldehyde. Methylated tau was de-salted using a Zebra spin desalting column (7K MWCO, Pierce) before being subjected to trypsin in-solution digestion and LC-MS/MS analysis.

Liquid Chromatography-Tandem Mass Spectrometry (LC-MS/MS)—

Mass spectrometric analysis of PHF-tau was performed using an LTQ ion trap mass spectrometer controlled by Xcalibur v. 1.4 software (Thermo Electron) coupled online to a nanoflow XTreme Simple L C system (CVC Micro-Tech) as previously described [Cripps D, Thomas S N, Jeng Y, Yang F, Davies P, Yang A J (2006) Alzheimer disease-specific conformation of hyperphosphorylated paired helical filament-Tau is polyubiquitinated through Lys-48, Lys-11, and Lys-6 ubiquitin conjugation. J Biol Chem 281:10825-10838, incorporated by reference herein in its entirety]. Briefly, peptides were either loaded onto a trap column (Agilent Zorbax C18 guard column, or Michrom Bioresources peptide cap trap) or loaded directly into the sample loop with 95% solvent A (2% acetonitrile, 0.1% formic acid) and 5% solvent B (95% acetonitrile, 0.1% formic acid). A 60 min linear gradient of 5-25% solvent B was used to elute the peptides from the reverse phase column (150 mm×75 μm, 5 μm 300 Å C18; CVC Micro-Tech).

The mass spectrometer was equipped with a nanospray ionization source (Thermo Electron) using an uncoated 10 μm i.d. SilicaTip PicoTip™ nanospray emitter (New Objective). The spray voltage of the mass spectrometer was 2.0 kV and the heated capillary temperature was 200° C. The top five ions in each MS1 scan were selected for MS/MS fragmentation. After ions were selected for MS/MS fragmentation twice within 30 sec, they were dynamically excluded for 30 sec. An MS3 scan was triggered if, among the three most abundant ions in the MS/MS scan, a neutral loss of 98, 49, or 32.7 Da (corresponding to a loss of $H_3PO_4$ from 1+, 2+, or 3+ precursor ions, respectively) was detected. Other mass spectrometric data generation parameters were as follows: collision energy 24% (35% for MS3 scans), MS scan range 400-1800 m/z, minimum MS signal intensity 500 counts, minimum MS/MS signal intensity 100 counts, and MS/MS activation time 120 ms (30 ms for MS3 scans).

Analysis of Mass Spectrometric Data—

Spectra were searched against a UniProtKB human protein database (version Oct. 5, 2010; 20,259 reviewed sequences; 75,498 non-reviewed sequences) using Bioworks 3.3.1 SP1 with the SEQUEST algorithm. Search parameters included 1.5 amu peptide mass tolerance, 1.0 amu fragment tolerance, static Cys +57 (carbamidomethylation) modification and the following differential modifications: Met +16 (oxidation); Ser, Thr, Tyr +80 (phosphorylation); Ser, Thr −18 (dehydroalanine and 2-aminodehydrobutyric acid, respectively); Lys, Asp, Glu +14 (monomethylation); Lys +28 (dimethylation); Lys +42 (trimethylation/acetylation); and Lys +114 (ubiquitylation). Fully enzymatic (trypsin or Lys-C) peptides with up to two missed cleavages and charge-state dependent cross correlation (XCorr) scores≥1.5, 2.5, and 3.0 for 1+, 2+, and 3+ peptides, respectively, and ΔCn>0.1 were considered as initial positive identifications. All MS/MS and MS3 spectra of identified post-translationally modified peptides from the initial screening were subjected to manual verification.

All raw data from this study are freely available at www.proteomeumb.org, which also serves as a data-sharing portal. The original raw data are also available from http://proteomecommons.org with the following Hash IDs: Tau trypsin digestion dataset: (Y297YWVSnnKcaY3jSnQkuCWj7tA1mls59uBBjjBpyqF5hOQ4ISmAuWNhvtdC1EQCsj5A7XFM0/3zj9YvVUlJlluuwcoAAAAAAAABrA==); Tau Lys-C digestion dataset: (pNmgHCue Fwyw3vtAgldKGatW5G8weUl7ArA/Fg+OIChNsahHAD GSEQp7iUAOzouc81DMfWpeq7li1pDcjOkrs1h9BHAAA AAAAAABpg==).

Immunohistochemistry—

Coronal hippocampal tissue sections were cut (20 μm thickness) and processed for immunohistochemistry as described previously [Funk K E, Mrak R E, Kuret J (2011) Granulovacuolar degeneration (GVD) bodies of Alzheimer's disease (AD) resemble late-stage autophagic organelles. Neuropathol Appl Neurobiol 37:295-306; Kannanayakal T J, Tao H, Vandre D D, Kuret J (2006) Casein kinase-1 isoforms differentially associate with neurofibrillary and granulovacuolar degeneration lesions. Acta Neuropathol 111:413-421, incorporated by reference herein in their entireties]. Sections were rehydrated in PBST (2.7 mM KCl, 0.14 M NaCl, 8.1 mM $Na_2HPO_4$, 0.1% Tween-20, pH 7.4) and fixed (10 min) in ice cold methanol. After 3×5 min rinses in PBST, sections were blocked (1 hr at 19° C.) with 5% goat serum diluted in PBST, then incubated (overnight at 4° C.) with primary antibodies diluted in 2.5% goat serum (Tau5, 1 μg/ml; Anti-meK, 0.3 μg/ml; ATB, 0.1 μg/ml). After washing in PBST (3×10 min), sections were incubated (1 hr at 19° C.) with fluorescent dye-labeled secondary antibodies (1.5 μg/ml Cy3-conjugated goat anti-rabbit IgG; 2 μg/ml Alexa Fluor 488-conjugated goat anti-mouse IgG). After washing in PBST (3×5 min), tissue was treated (10 min at 19° C.) with 0.1% Sudan Black B (EM Diagnostics, Gibbstown, N.J.) in 80% ethanol to suppress lipofuscin autofluorescence [Schnell S A, Staines W A, Wessendorf M W (1999) Reduction of lipofuscin-like autofluorescence in fluorescently labeled tissue. J Histochem Cytochem 47:719-730, incorporated by reference herein in its entirety]. Sections were then washed (2×5 min) in PBST and once for 5 min in PB (33 mM $NaH_2PO_4$, 162 mM $Na_2HPO_4$, pH 7.4). Coverslips were mounted with Vectashield (Vector Laboratories, Burlingame, Calif.) and sealed with clear nail enamel. Labeled sections were viewed in a Leica TCS SL laser-scanning confocal system (40× oil HCX Plan Apo CS 0.75-1.25 NA or 100× oil HCX Plan Apo CS 0.70-1.40 NA objective lens) operated at wavelengths optimized for simultaneous detection of Alexa Fluor 488 ($\lambda_{ex}$=488 nm; $\lambda_{em}$=500-530 nm), and Cy3 ($\lambda_{ex}$=543 nm; $\lambda_{em}$=560-600 nm). Long wavelength fluorescence ($\lambda_{ex}$=633 nm; $\lambda_{em}$=650-740 nm) also was monitored to assess autofluorescence intensity. Digital confocal images were captured at 1× and 3× digital zoom, and stored in Tagged Image Format. Both secondary antibodies displayed minimal non-specific staining under these conditions as determined by immunostaining in the absence of primary antibodies.

Analytical Methods—

The proportion of methyl-positive NFTs was estimated using the Wilson score method [Funk K E, Mrak R E, Kuret J (2011) Granulovacuolar degeneration (GVD) bodies of Alzheimer's disease (AD) resemble late-stage autophagic organelles. Neuropathol Appl Neurobiol 37:295-306; Newcombe R G (1998) Improved confidence intervals for the difference between binomial proportions based on paired data. Stat Med 17:2635-2650, incorporated by reference herein in their entireties]. At least 15 lesions, defined as Tau-positive bodies at least 7 μm in both length and width, were counted from at least 5 fields of each case so that the 95% confidence interval for colocalization was <15%. Overall mean colocalization was then calculated as the average of all three biological replicate means and reported±standard deviation.

Results

Non-Pathological Tau is Methylated in its Terminal Projection Domains and Microtubule Binding Domains.

To identify sites of Lys methylation in non-pathological tau, neuropathologically normal brain tissue was processed for tau enrichment. The normal tau was subjected to analysis by LC-MS/MS, and interrogated using the SEQUEST database search algorithm programmed to identify unmodified Lys residues along with sites of monomethylation (K+14), dimethylation (K+28), trimethylation (K+42), and acetylation (also K+42). Sequence coverage in these datasets included 33 out of the 44 Lys residues present in the longest form of human brain tau protein (2N4R tau, FIG. 1). These search conditions found 13 unique sites of modification with evidence of mono- and di-methylation (see Table 1 below). Three sites of methylation are found in the N- or C-terminal projection domains, while nine are found within the microtubule binding region of the protein. Notably, K311, which was found in both di- and tri-methylated forms, resides within the "PHF6" sequence that modulates fibrillization rate of recombinant monomeric 4R tau in vitro [Iliev A I, Ganesan S, Bunt G, Wouters F S (2006) Removal of pattern-breaking sequences in microtubule binding repeats produces instantaneous tau aggregation and toxicity. J Biol Chem 281:37195-37204; Li W, Lee V M (2006) Characterization of two VQIXXK motifs for tau fibrillization in vitro. Biochemistry 45:15692-15701; von Bergen M, Friedhoff P, Biernat J, Heberle J, Mandelkow E M, Mandelkow E (2000) Assembly of tau protein into Alzheimer paired helical filaments depends on a local sequence motif ((306)VQIVYK (311)) forming beta structure. Proc Natl Acad Sci USA 97:5129-5134, incorporated by reference herein in their entireties]. Together these data reveal that tau is normally a highly methylated protein in vivo.

TABLE 1

Lys methylation sites identified on normal tau. Trypsin in-gel digests of normal tau were analyzed by nanoflow LC-MS/MS and the data were searched against a human database using Bioworks with the SEQUEST algorithm. Amino acids in bold indicate identified methylated Lys residues. Amino acid (aa) residues are based on the human tau isoform with NCBI accession number NP_005901. Abbreviations for the tau domains are as follows: N = N-terminal projection domain; P = Pro-rich region; M = microtubule-binding domain; R1, R2, R3, R4 = repeat regions 1, 2, 3, and 4 respectively; C = C-terminal projection domain. Abbreviations for modifications are as follows: me1, monomethyl; me2, dimethyl.

| aa residues | Peptide | Methyl site | Modification | Tau domain |
|---|---|---|---|---|
| 24-44 | **K**DQGGYTMHQDQEDTDAGLK [SEQ. ID. NO. 2] | K24 | me2 | N |
| 25-44 | DQGGYTMHQDQEGDTDAGL**K** [SEQ. ID. NO. 3] | K44 | me1 | N |

TABLE 1-continued

Lys methylation sites identified on normal tau. Trypsin in-gel digests of normal tau were analyzed by nanoflow LC-MS/MS and the data were searched against a human database using Bioworks with the SEQUEST algorithm. Amino acids in bold indicate identified methylated Lys residues. Amino acid (aa) residues are based on the human tau isoform with NCBI accession number NP_005901. Abbreviations for the tau domains are as follows: N = N-terminal projection domain; P = Pro-rich region; M = microtubule-binding domain; R1, R2, R3, R4 = repeat regions 1, 2, 3, and 4 respectively; C = C-terminal projection domain. Abbreviations for modifications are as follows: me1, monomethyl; me2, dimethyl.

| aa residues | Peptide | Methyl site | Modification | Tau domain |
|---|---|---|---|---|
| 243-257 | LQTAPVPMPDL**K**NVK [SEQ. ID. NO 4] | K254 | me2 | M, R1 |
| 258-267 | S**K**IGSTENLK [SEQ. ID. NO. 5] | K259 | me1 | M, R1 |
| 281-290 | **K**LDLSNVQSK [SEQ. ID. NO. 6] | K281 | me2 | M, R2 |
| 281-290 | KLDLSNVQS**K** [SEQ. ID. NO. 7] | K290 | me2 | M, R2 |
| 306-317 | VQIVY**K**PVDLSK [SEQ. ID. NO. 1] | K311 | me2 | M, R3, PHF6 |
| 306-317 | VQIVYKPVDLS**K** [SEQ. ID. NO. 8] | K317 | me2 | M, R3 |
| 322-343 | CGSLGNIHHKPGGGQVEV**K**SE**K** [SEQ. ID. NO. 9] | K340, K343 | me2 | M, R4 |
| 350-369 | VQS**K**IGSLDNITHVPGGGNK [SEQ. ID. NO. 10] | K353 | me2 | M, R4 |
| 354-369 | IGSLDNITHVPGGGN**K** [SEQ. ID. NO 11] | K369 | me2 | M, R4 |

PHF-Tau is Methylated in its N-Terminal Projection and Microtubule Binding Domains.

To identify sites of Lys modification in PHF-tau, previously collected MS datasets obtained from two independent preparations of authentic AD-brain derived PHFs [digested with either trypsin or Lys-C proteases; [Cripps D, Thomas S N, Jeng Y, Yang F, Davies P, Yang A J (2006) Alzheimer disease-specific conformation of hyperphosphorylated paired helical filament-Tau is polyubiquitinated through Lys-48, Lys-11, and Lys-6 ubiquitin conjugation. J Biol Chem 281:10825-10838, incorporated by reference herein in its entirety]] were interrogated using the SEQUEST database search algorithm programmed to identify unmodified Lys residues along with sites of monomethylation (K+14), dimethylation (K+28), trimethylation (K+42), acetylation (also K+42), and ubiquitylation (K+114). Sequence coverage in these datasets included 25 out of the 44 Lys residues present in the longest form of human brain tau protein (2N4R tau, FIG. 1). Although these search conditions confirmed three sites of ubiquitylation in the microtubule binding repeat region [K254, K311, and K353; [Cripps D, Thomas S N, Jeng Y, Yang F, Davies P, Yang A J (2006) Alzheimer disease-specific conformation of hyperphosphorylated paired helical filament-Tau is polyubiquitinated through Lys-48, Lys-11, and Lys-6 ubiquitin conjugation. J Biol Chem 281:10825-10838, incorporated by reference herein in its entirety]], no evidence for either K+28 or K+42 masses was found, indicating that dimethyl-Lys, trimethyl-Lys, and acetyl-Lys were not present in the coverage area at the level of detection available in our datasets. However, robust monomethylation was identified at seven sites spanning the tau sequence (see Table 2, below). Three of the sites (K163, K174, and K180) reside within the proline-rich region of the tau N-terminal projection domain, which mediates interactions with microtubule-associated proteins such as actin [He H J, Wang X S, Pan R, Wang D L, Liu M N, He R Q (2009) The proline-rich domain of tau plays a role in interactions with actin. BMC Cell Biol 10:81, incorporated by reference herein in its entirety] and the Src homology 3 domain of plasma membrane-associated proteins including Src family kinases [Lee G, Newman S T, Gard D L, Band H, Panchamoorthy G (1998) Tau interacts with src-family non-receptor tyrosine kinases. J Cell Sci 111:3167-3177, incorporated by reference herein in its entirety] and phospholipase Cγ [Reynolds C H, Garwood C J, Wray S et al (2008) Phosphorylation regulates tau interactions with Src homology 3 domains of phosphatidylinositol 3-kinase, phospholipase Cgamma1, Grb2, and Src family kinases. J Biol Chem 283:18177-18186, incorporated by reference herein in its entirety]. In contrast, K254, K267, and K290 are part of the first and second repeats of the microtubule-binding domain. Together these data reveal that PHF-tau is monomethylated in disease, and that the major occupied sites distribute across protein segments known to mediate tau-protein interactions (including tubulin binding and self association).

TABLE 2

Lys methylation sites identified on PHF-tau. Lys-C and trypsin in-solution digests of PHF-tau were analyzed by nanoflow LC-MS/MS and the data were searched against a human database using Bioworks with the SEQUEST algorithm. Amino acids in bold indicate identified monomethylated Lys residues. Amino acid (aa) residues are based on the human tau isoform with NCBI accession number NP_005901. Abbreviations for the tau domains are as follows: N = N-terminal projection domain; P = Pro-rich region; M = microtubule-binding domain; R1, R2 = repeat regions 1 and 2, respectively.

| aa residues | Peptide | Methyl site | Charge state(s) | Tau domain | XCorr score | Δ Cn |
|---|---|---|---|---|---|---|
| 25-44 | DQGGYTMHQDQEGDTDAGLK [SEQ. ID. NO. 3] | K44 | 3+ | N | 4.07 | 0.16 |
| 151-163 | IATPRGAAPPGQK [SEQ. ID. NO. 12] | K163 | 2+ | N, P | 3.28 | 0.42 |
| 164-174 | GQANATRIPAK [SEQ. ID. NO. 13] | K174 | 2+ | N, P | 3.03 | 0.28 |
| 175-180 | TPPAPK [SEQ. ID. NO. 14] | K180 | 1+ | N, P | 1.59 | 0.33 |
| 241-254 | SRLQTAPVPMPDLK [SEQ. ID. NO. 15] | K254 | 2+/3+ | M, R1 | 3.71/3.55 | 0.41/0.24 |
| 258-267 | SKIGSTENLK [SEQ. ID. NO. 16] | K267 | 2+ | M, R1 | 3.14 | 0.40 |
| 281-290 | KLDLSNVQSK [SEQ. ID. NO. 7] | K290 | 2+ | M, R2 | 3.56 | 0.28 |

To quantitatively assess the relative abundances of methylated, ubiquitylated and unmodified PHF-tau peptides, data were subjected to spectral counting, which measures the number of times a peptide is identified by MS/MS. Because spectral counts correlate linearly with protein abundance [Liu H, Sadygov R G, Yates J R, 3rd (2004) A model for random sampling and estimation of relative protein abundance in shotgun proteomics. Anal Chem 76:4193-4201, incorporated by reference herein in its entirety], they have been employed for relative quantification in many label-free proteomic studies [Choi H, Fermin D, Nesvizhskii A I (2008) Significance analysis of spectral count data in label-free shotgun proteomics. Mol Cell Proteomics 7:2373-2385; Old W M, Meyer-Arendt K, Aveline-Wolf L et al (2005) Comparison of label-free methods for quantifying human proteins by shotgun proteomics. Mol Cell Proteomics 4:1487-1502; Sardiu M E, Cai Y, Jin J et al (2008) Probabilistic assembly of human protein interaction networks from label-free quantitative proteomics. Proc Natl Acad Sci USA 105:1454-1459; Schmidt M W, Houseman A, Ivanov A R, Wolf D A (2007) Comparative proteomic and transcriptomic profiling of the fission yeast *Schizosaccharomyces pombe*. Mol Syst Biol 3:79; Zhang B, VerBerkmoes N C, Langston M A, Uberbacher E, Hettich R L, Samatova N F (2006) Detecting differential and correlated protein expression in label-free shotgun proteomics. J Proteome Res 5:2909-2918, incorporated by reference herein in their entireties]. Relative abundance was calculated by dividing the spectral count of the modified peptide by the sum of the spectral counts of the modified and unmodified form of the peptide. Results showed that monomethylation relative abundance varied among sites, from 67% (Lys180 and Lys267) to 12% (Lys290) (see Table 3; FIG. 2). The relative abundance of ubiquitylation varied from 33% (Lys311) to 1% (Lys254) (FIG. 2).

TABLE 3

Relative abundances of methylated and ubiquitylated PHF-tau peptides as assessed by spectral counts. Spectral counts are defined as the number of times a peptide was identified by MS/MS. Amino acids in bold indicate identified methylated Lys residues. n.d. = not detected. % Modified is calculated based on the following spectral counts: modified peptide/(modified peptide + un-modified peptide). me, methylation; ub, ubiquitylation.

| aa residues | Peptide | Modification site | Spectral count Modified | Spectral count Unmodified | Spectral count Total | % Modified |
|---|---|---|---|---|---|---|
| 25-44 | DQGGYTMHQDQEGDTDAGLK [SEQ. ID. NO. 2] | me-K44 | 11 | 18 | 29 | 38% |
| 151-163 | IATPRGAAPPGQK [SEQ. ID. NO. 12] | me-K163 | 2 | 6 | 8 | 25% |
| 164-174 | GQANATRIPAK [SEQ. ID. NO. 13] | me-K174 | 2 | n.d. | 2 | n.d. |

TABLE 3-continued

Relative abundances of methylated and ubiquitylated PHF-tau peptides as assessed by spectral counts. Spectral counts are defined as the number of times a peptide was identified by MS/MS. Amino acids in bold indicate identified methylated Lys residues. n.d. = not detected. % Modified is calculated based on the following spectral counts: modified peptide/(modified peptide + un-modified peptide). me, methylation; ub, ubiquitylation.

| aa residues | Peptide | Modification site | Spectral count Modified | Unmodified | Total | % Modified |
|---|---|---|---|---|---|---|
| 175-180 | TPPAP**K** [SEQ. ID. NO. 14] | me-K180 | 2 | 1 | 3 | 67% |
| 241-254 | SRLQTAPVPMPDL**K** [SEQ. ID. NO. 15] | me-K254 | 17 | 24 | 41 | 41% |
| 243-257 | LQTAPVPMPDL**K**NVK [SEQ. ID. NO. 4] | ub-K254 | 2 | 188 | 190 | 1% |
| 258-267 | SKIGSTENL**K** [SEQ. ID. NO. 16] | me-K267 | 6 | 3 | 9 | 67% |
| 281-290 | KLDLSNVQS**K** [SEQ. ID. NO. 7] | me-K290 | 2 | 14 | 16 | 12% |
| 299-317 | HVPGGGSVQIVY**K**PVDLSK [SEQ. ID. NO. 17] | ub-K311 | 5 | 10 | 15 | 33% |
| 350-369 | VQS**K**IGSLDNITHVPGGGNK [SEQ. ID. NO. 10] | ub-K353 | 2 | 49 | 51 | 4% |

Methyl-Lys Immunoreactivity Associates with the Neurofibrillary Lesions of AD.

Figure 3:
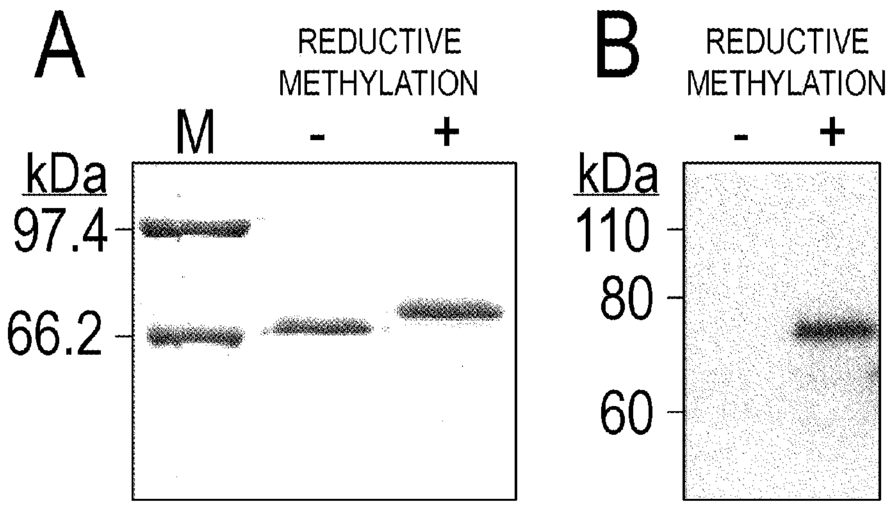
FIG. 3 (having panels A and B) are photographs showing the specificity of anti-meK antibody. Aliquots of unmodified (−) and in vitro methylated (+) 2N4R tau were separated by SDS-PAGE (8% polyacrylamide) and either (1) stained with Coomassie Blue (500 ng tau proteins)—as shown in panel A, or (2) subjected to immunoblot analysis with anti-meK antibody (100 ng tau protein)—as shown in panel B. Molecular mass calibration markers (M) are shown in units of kDA. High-stoichiometry reductive methylation reduced recombinant 2N4R migration on SDS-PAGE. The anti-meK antibody was specific for methylated tau under these conditions.

In AD, PHF-tau accumulates within neurofibrillary lesions associated with neuronal cell bodies (NFTs), neuronal processes (neuropil threads), and the dystrophic neurites of neuritic plaques [Buee L, Bussiere T, Buee-Scherrer V, Delacourte A, H of PR (2000) Tau protein isoforms, phosphorylation and role in neurodegenerative disorders. Brain Res Brain Res Rev 33:95-130, incorporated by reference herein in its entirety]. To determine whether tau methylation correlated spatially with neurofibrillary pathology, sections of AD brain hippocampus were probed with a polyclonal antibody that labels meK-containing proteins. The specificity of this reagent was first tested on recombinant 2N4R tau preparations that were subjected to reductive methylation in vitro (see materials and methods). When subjected to SDS-PAGE, both non-methylated and methylated 2N4R tau migrated as single species, with the latter undergoing a band shift to 73 kDa (FIG. 3A). Rabbit polyclonal anti-meK antibody strongly labeled this species but not nonmethylated 2N4R tau, confirming that it specifically binds methylated protein (FIG. 3B).

Figure 4:
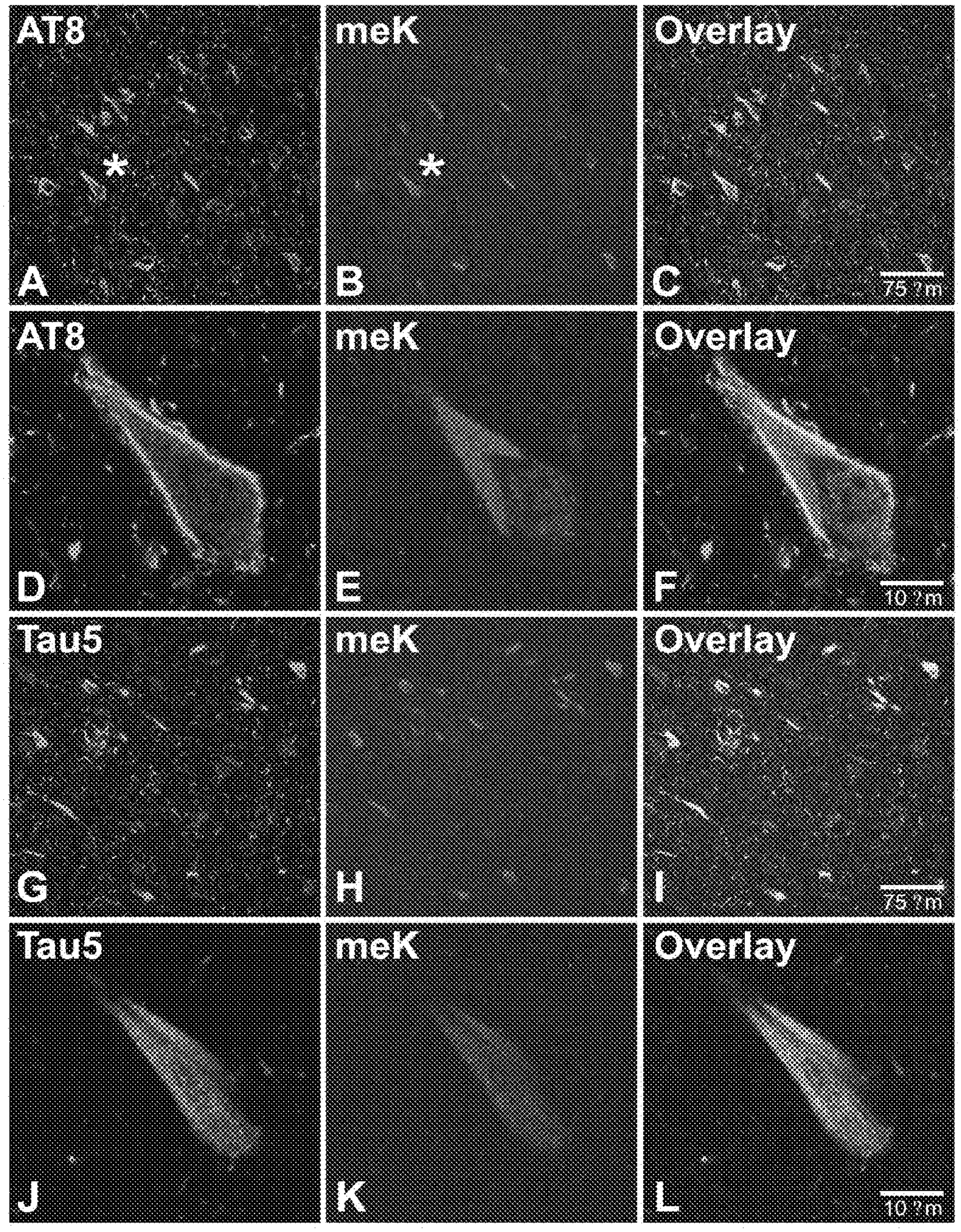
FIG. 4 (having panels A-L) is a series of microphotographs showing that anti-meK immunoreactivity colocalizes with neurofibrillary lesions in AD hippocampus. Double-label confocal images of hippocampal sections (CA1 region) stained with anti-tau mouse monoclonal antibodies AT8 (panels A, D; green channel) or Tau5 (panels G, J; green channel) along with the rabbit anti-meK antibody (panels B, E, H, K; red channel). Low magnification images (40× objective, 1× zoom) show colocalization of anti-meK immunoreactivity with NFTs (panels A, B; asterisks) and neuritic plaques (panels G, H; arrows). High magnification images (100× objective, 3× zoom) show morphology of typical NFTs (panels D, E and J, K). Image overlays highlight pixel overlap between anti-meK and AT8 (F) and Tau5 (L) immunoreactivity. Anti-meK immunoreactivity colocalized extensively with NFTs in all fields examined.

The antibody was then applied to double-label confocal immunofluorescence studies using hippocampal brain sections prepared from three late-stage AD cases (Table 3) along with well-characterized anti-tau antibodies AT8 and Tau5 [Braak H, Alafuzoff I, Arzberger T, Kretzschmar H, Del Tredici K (2006) Staging of Alzheimer disease-associated neurofibrillary pathology using paraffin sections and immunocytochemistry. Acta Neuropathol 112:389-404; LoPresti P, Szuchet S, Papasozomenos S C, Zinkowski R P, Binder L I (1995) Functional implications for the microtubule-associated protein tau: localization in oligodendrocytes. Proc Natl Acad Sci USA 92:10369-10373, incorporated by reference herein in their entireties]. These antibodies were chosen for analysis because their epitopes are present during all phases of NFT development, including the early pre- and intracellular-NFT stages [Shimazaki M, Nakano H, Kobayashi K (2005) Correlation between tau phosphorylation sites and tangle morphology in Alzheimer's disease. Psychogeriatrics 5:22-35, incorporated by reference herein in its entirety]. Both AT8 (FIG. 4A, D) and Tau 5 (FIG. 4G, J) strongly labeled neurofibrillary lesions in these sections, including NFTs, neuropil threads, and neuritic plaques. At high magnification, NFTs immunolabeled with Tau5 displayed a fibrillar pattern throughout the lesions (FIG. 4J), while those labeled with AT8 also displayed a pattern of intense immunoreactivity enriched on the outer rims of the lesions (FIG. 4D). Rim staining, which has been seen previously with AT8 [Ikonomovic M D, Abrahamson E E, Isanski B A et al (2006) X-34 labeling of abnormal protein aggregates during the progression of Alzheimer's disease. Methods Enzymol 412:123-144, incorporated by reference herein in its entirety], was particularly conspicuous at low fluorescence gain. In contrast, anti-meK immunoreactivity appeared diffusely distributed throughout the sections (FIG. 4B, E, H, K), with the most intense labeling correlating with both AT8- and Tau5-stained lesions, and with the pattern of reactivity resembling that of Tau5 with fibrillar staining throughout the lesion (FIG. 4C, F, I, L). Although background fluorescence was too high to detect neuropil threads, colocalization with particularly large or intense dystrophic neurites was occasionally seen (FIG. 4H-J). NFT labeling was robust, however, and so colocalization of meK immunoreactivity with this lesion was quantified in hippocampus CA1 region. Results showed that the majority of NFTs labeled with anti-meK antibody in all three cases (see Table 4, below). Overall, anti-meK colocalization with AT8-labeled NFTs averaged 81±19% (SD, n=3 cases) whereas colocalization with Tau5-labeled NFTs averaged 77±22% (SD, n=3 cases). Together these data show that the methylation of PHF-tau identified through mass spectrometry is widespread in this affected brain region, with most NFTs harboring anti-meK immunoreactivity in late-stage AD.

TABLE 4

Case demographics and marker colocalization in hippocampus CA1 region.

| Case (#) | Age (yrs) | Gender | PMI (hr) | Diagnosis | meK/AT8 colocalization ± SE | n | meK/Tau5 colocalization ± SE | n |
|---|---|---|---|---|---|---|---|---|
| 1 | 61 | M | 5.3 | AD; Braak stage V-VI | 93.8 ± 5.9% | 16 | 91.7 ± 5.5% | 36 |
| 2 | 81 | F | — | AD; Braak stage V-VI, vascular involvement | 89.7 ± 6.9% | 39 | 88.9 ± 7.5% | 36 |
| 3 | 86 | M | 3.2 | AD, Braak stage V-VI | 58.6 ± 11.5% | 70 | 51.5 ± 10.2% | 97 |

Discussion

Although certain familial tauopathies result from missense mutations in the tau gene (MAPT), AD pathogenesis is not associated with changes in tau amino acid sequence. Rather, tau lesion formation in sporadic AD is accompanied by PTMs that contribute to pathogenesis by modulating tau function, stability, and aggregation propensity. Because neurofibrillary lesion density correlates with neurodegeneration [Gomez-Isla T, Price J L, McKeel D W, Jr., Morris J C, Growdon J H, Hyman B T (1996) Profound loss of layer II entorhinal cortex neurons occurs in very mild Alzheimer's disease. J Neurosci 16:4491-4500; Josephs K A, Whitwell J L, Ahmed Z et al (2008) Beta-amyloid burden is not associated with rates of brain atrophy. Ann Neurol 63:204-212, incorporated by reference herein in their entireties] and cognitive decline [Ghoshal N, Garcia-Sierra F, Wuu J et al (2002) Tau conformational changes correspond to impairments of episodic memory in mild cognitive impairment and Alzheimer's disease. Exp Neurol 177:475-493; Giannakopoulos P, Herrmann F R, Bussiere T et al (2003) Tangle and neuron numbers, but not amyloid load, predict cognitive status in Alzheimer's disease. Neurology 60:1495-1500; Royall D R, Palmer R, Mulroy A R et al (2002) Pathological determinants of the transition to clinical dementia in Alzheimer's disease. Exp Aging Res 28:143-162, incorporated by reference herein in their entireties], a high priority in the AD field is to identify the PTM signature that drives neurofibrillary lesion formation in sporadic disease. Here, it was determined that tau is normally a highly methylated protein at no less than seventeen distinct sites. These sites of modification change or become demethylated with the onset of pathogenesis. Due to the high local concentration of tau in neurofibrillary tangles, even the modest methylation can be visualized by immunohistochemistry, and by late Braak stage, the modification is widespread among tau lesions and found in the majority of NFTs in the CA1 region of AD hippocampus. These findings suggest that changes in the pattern of tau methylation are associated with its pathogenicity.

In conclusion, the biophysical evidence from the study shows that thirteen Lys residues (K24, K44, K254, K259, K281, K 290, K311, K 317, K 340, K 343, K353, K369, K395) in tau enriched from pathologically normal brain are subject to varying degrees of methylation. Furthermore, seven Lys residues (K44, K163, K174, K180, K254, K267, and K290) in PHF-tau immunopurified from AD brain are monomethylated. Moreover, Lys methylation is present in intact tissue sections and is associated with the neurofibrillary lesions of AD. Without being bound by any theory, this is likely because of the high local concentration of tau in neurofibrillary tangles.

Example 2

Alzheimer's disease (AD) is defined in part by the appearance of intracellular inclusions composed of the microtubule associated protein tau. The mechanisms that drive tau aggregation in the highly prevalent sporadic form of AD are not fully understood, but appear to involve abnormal post-translational modifications. To gain insight into the modifications that accompany tau lesion formation in AD, a preliminary structural analysis of tau aggregates isolated from authentic disease tissue specimens using mass spectrometry methods was conducted. The results revealed that a previously unrecognized tau modification, lysine methylation, copurified with tau aggregates. The methylation signature involved sites that are known to mediate tau ubiquitylation and other post-translational modifications, suggesting that methylation is a candidate modification for influencing tau aggregation and toxicity in disease. To extend the correlation between methylation occupancy and aggregation state, the modification state of soluble tau protein isolated from cognitively normal human brain was investigated, again using proteomic methods. Results showed that normal soluble tau was hypermethylated relative to AD-derived tau in its microtubule-binding repeat region. These data establish Lys methylation as normal tau post-translational modification in human brain. When purified recombinant human tau was subjected to Lys methylation in vitro, its tubulin assembly promoting activity was retained, but its aggregation propensity was greatly attenuated. Thus, it is determined that Lys methylation protects against pathological tau aggregation during normal aging, and that tau methylation modification enzymes may be tractable targets for disease modifying therapies focused on halting neurofibrillary lesion formation in AD.

Introduction

In order to determine the PTM signature most closely associated with NFT formation, authentic paired helical filaments (PHFs) immunopurified from AD brain were mapped, using mass spectrometry methods. Recently, the discovery of Lys methylation as a previously unidentified PTM of PHF-tau was reported [Thomas S N, et al. (2012) Dual modification of Alzheimer's disease PHF-tau protein by lysine methylation and ubiquitylation: a mass spectrometry approach. Acta Neuropathol. (Berl). 123(1):105-117]. Here, the characterization of tau methylation to soluble tau protein enriched from pathologically normal human brain is extended. Analysis revealed that in contrast to tau phosphorylation, which increases in disease, Lys residues are hypomethylated in the diseased state. Furthermore, using in vitro biochemical methods, the effect of tau methylation on its normal function of binding and stabilizing microtubules and also the effect of methylation on tau aggregation propensity.

Materials and Methods

Materials

Recombinant polyhistidine-tagged 2N4R tau was prepared as described previously [Necula M & Kuret J (2004) A static laser light scattering assay for surfactant-induced tau fibrillization. Anal Biochem 333(2):205-215; Carmel G, Mager E M, Binder L I, & Kuret J (1996) The structural basis of monoclonal antibody Alz50's selectivity for Alzheimer's disease pathology. J Biol Chem 271(51):32789-32795, incorporated by reference herein in their entireties]. [$^{14}$C]Formaldehyde was obtained from Perkin Elmer (Waltham, Mass., USA) with a specific activity of 54.8 Ci/mol. Purified tubulin was purchased from Cytoskeleton (Denver, Colo., USA). Aggregation inducer Thiazine red (Chemical Abstract Service registry number 2150-33-6) was obtained from TCI America (Portland, Oreg., USA). Formvar/carbon-coated copper grids, glutaraldehyde, and uranyl acetate were obtained from Electron Microscopy Sciences (Fort Washington, Pa., USA).

Preparation of Tau from Human Control Brain and HEK-293 Cells

This study used only archival, de-identified post mortem brain tissue samples from autopsies performed with informed consent of each patient or relative via procedures approved by the relevant institutional committees (Ohio State University, Columbus, Ohio). Tau was enriched from brain tissue using methods detailed previously [Ksiezak-Reding H, Liu W K, & Yen S H (1992) Phosphate analysis and dephosphorylation of modified tau associated with paired helical filaments. Brain Res 597(2):209-219, incorporated by reference herein in its entirety]. Briefly, brain tissue obtained at autopsy lacking neuropathology was homogenized in 5 volumes of homogenization buffer (by weight) including phosphatase inhibitors (20 mM 2-(N-morpholino)ethanesulfonic acid (MES)/NaOH, pH 6.8, 80 mM NaCl, 1 mM $MgCl_2$, 2 mM EGTA, 0.1 mM EDTA, 1 mM PMSF, 10 mM $Na_4O_7P_2$, 20 mM NaF, 1 mM $Na_3VO_4$). The homogenate was separated by centrifugation (20 min at 27,000×g). The supernatant was subjected to heat treatment (10 min boiling) in the presence of 0.5 M NaCl and 2% 2-mercaptoethanol. After heat treatment, the supernatant was collected (20 min at 27,000×g) and treated with 2.5% (final concentration) of perchloric acid to remove acid-insoluble non-tau material. After centrifugation, the acid-soluble extract was treated with trichloroacetic acid (TCA) up to 20% (w/v) and the TCA-precipitated proteins were washed twice with cold acetone and allowed to dry. The TCA pellets were suspended in a buffer suitable for analysis.

Preparation of tetracycline-inducible 2N4R-expressing HEK-293 cells (TRex-293) was described previously [Bandyopadhyay B, Li G, Yin H, & Kuret J (2007) Tau aggregation and toxicity in a cell culture model of tauopathy. J Biol Chem 282(22):16454-16464, incorporated by reference herein in its entirety]. Cells were maintained in Dulbecco's modified Eagle's medium supplemented with 10% fetal bovine serum, 100 units/ml penicillin G, 270 μM amphotericin B, and 170 μM streptomycin (37° C. with 5% $CO_2$). Cells were grown under selection with 12 μM blasticidin, and treated with 2.2 μM tetracycline for 5 days to induce tau expression. For tau enrichment cells were rinsed once in cold phosphate-buffered saline (2.7 mM KCl, 0.14 M NaCl, 8.1 mM $Na_2HPO_4$, pH 7.4), collected with cell lifters, and centrifuged at 3000×g for 5 min. Harvested cells were then homogenized in 5 volumes of homogenization buffer (by weight) and processed as detailed above.

Liquid Chromatography-Tandem Mass Spectrometry (LC-MS/MS)

Mass spectrometric analysis of tau enriched from cognitively normal brain was performed as previously described [Cripps D, et al. (2006) Alzheimer disease-specific conformation of hyperphosphorylated paired helical filament-Tau is polyubiquitinated through Lys-48, Lys-11, and Lys-6 ubiquitin conjugation. J Biol Chem 281(16):10825-10838; Thomas S N, et al. (2012) Dual modification of Alzheimer's disease PHF-tau protein by lysine methylation and ubiquitylation: a mass spectrometry approach. Acta Neuropathol 123(1):105-117, incorporated by reference herein in their entireties].

Reductive Methylation of Recombinant Human 2N4R Tau

Reductive methylation was done as described previously with minor modifications [Thomas S N, et al. (2012) Dual modification of Alzheimer's disease PHF-tau protein by lysine methylation and ubiquitylation: a mass spectrometry approach. Acta Neuropathol 123(1):105-117; Jentoft N & Dearborn D G (1979) Labeling of proteins by reductive methylation using sodium cyanoborohydride. J Biol Chem 254(11):4359-4365, incorporated by reference herein in their entireties]. 2N4R tau was diluted to a final concentration of 20 μM in 0.1 M $Na_3C_6H_5O_7$, pH 6, 0.1 M $NaBH_3CN$, and 5 mM formaldehyde. For determination of methyl group incorporation, [$^{14}$C]formaldehyde was diluted to a final specific activity of 0.88 Ci/mol. Reaction proceeded at 22° C. for up to 60 min.

For analysis of radiolabel incorporation, products were separated from reactants by protein desalting spin columns (Pierce, Rockford, Ill., USA) in 10 mM HEPES, pH 7.4, 50 mM NaCl. 20 μl of reaction product was added to 5 ml scintillation fluid (Cytoscint, Cole-Parmer, Vernon Hills, Ill., USA) and radioactive counts measured. Reactions and measurements were done in triplicate and are reported as mean±standard deviation (SD).

For mass spectrometry and biochemical analyses, reaction was prepared as described above with unlabeled formaldehyde. Methylated tau used for mass spectrometry samples were separated from reactants using protein desalting spin columns with 50 mM NaH3HCO$_4$, pH 7.8. Methylated tau used for biochemical analysis was prepared as described above, then stopped by addition of 50 mM glycine, and the products were then separated from reactants with disposable chromatography columns (BioRad, Hercules, Calif., USA) in low salt assembly buffer (10 mM HEPES, pH 7.4, 50 mM NaCl). Fractions were collected as they eluted from the column and assayed for protein content by absorbance at 280 nm. When necessary, fractions were concentrated using Centricon Centrifugal Filter Units (Millipore, Billerica, Mass., USA). Protein concentration was analyzed by bicinchroninic acid assay (Pierce, Rockford, Ill., USA) in triplicate (not shown).

Tubulin Polymerization Assay

Tubulin polymerization assay was done as classically described [Bandyopadhyay B, Li G, Yin H, & Kuret J (2007) Tau aggregation and toxicity in a cell culture model of tauopathy. J Biol Chem 282(22):16454-16464; Mitchison T & Kirschner M (1984) Microtubule assembly nucleated by isolated centrosomes. Nature 312(5991):232-237, incorporated by reference herein in their entireties]. Either unmodified or reductively methylated tau (2 μM) was incubated with 9 μM tubulin dimer in BRB80 with 1 mM DTT, 1 mM guanosine triphosphate, at 37° C. The time course of polymerization was followed by measuring absorbance at 340 nm every 1 min for 60 min using a Cary50 UV-V is Spectrophotometer (Agilent, Santa Clara, Calif., USA) with a Peltier single cell temperature control accessory. Change in absorbance at 340 nm was graphed as a function of time and fit to an exponential rise to max function in SigmaPlot to calculate the rate and extent of polymerization. Assay and fittings were done in triplicate and parameters were averaged to yield a mean±SD. Alternatively, Δ340 nm data points of each of three trials were averaged and plotted as a function of time±SD.

Tau Fibrillization Assay

Tau filaments were formed from purified tau incubated without agitation in assembly buffer (10 mM HEPES, pH 7.4, 100 mM NaCl, and 5 mM DTT) for up to 24 h (unless otherwise specified) at 37° C. Aggregation was initiated with Thiazine red (100 μM final concentration). Reactions were terminated with 2% glutaraldehyde, adsorbed to Formvar/carbon-coated copper grids, stained with 2% uranyl acetate, and viewed in a Tecnai G2 Spirit BioTWIN transmission electron microscope (FEI, Hillsboro, Oreg., USA) operated at 80 kV and 16,000-60,000× magnification. At least three viewing fields were captured for each reaction condition in which filaments>10 nm in length were counted and quantified with ImageJ. Total filament lengths of all resolved filaments per field are reported±SD.

Critical Concentration

Critical concentrations (Kcrit) were determined by inverse prediction of the abscissa intercept (xˆ) of a plot of the concentration dependence of tau aggregation, as described previously [Congdon E E, et al. (2008) Nucleation-dependent tau filament formation: the importance of dimerization and an estimation of elementary rate constants. J Biol Chem 283(20):13806-13816, incorporated by reference herein in its entirety] using the Taylor series expansion [Rice J A (2007) Mathematical statistics and data analysis (Thomson Brooks/Cole, Belmont, Calif.) 3rd Ed pp xvi, 603, A663, incorporated by reference herein in its entirety]:

$$\hat{x} = \frac{\mu_y}{\mu_x} + \frac{1}{\mu_x^2}\left(\sigma_x^2\frac{\mu_y}{\mu_x} - \sigma_x\sigma_y r\right) \quad \text{Eq. 1}$$

Where μy±σy is the ordinate intercept±SEE, $\mu_x \pm \sigma_x$ is the regression slope±SEE, and r is the regression correlation coefficient. The variance ($S^2$) was calculated as [Rice J A (2007) *Mathematical statistics and data analysis* (Thomson Brooks/Cole, Belmont, Calif.) 3rd Ed pp xvi, 603, A663, incorporated by reference herein in its entirety]:

$$S^2 = \frac{1}{\mu_x^2}\left(\sigma_x^2\frac{\mu_y^2}{\mu_x^2} + \sigma_y^2 - 2\sigma_x\sigma_y r\frac{\mu_y}{\mu_x}\right) \quad \text{Eq. 2}$$

Dissociation Kinetics

Assembled tau filaments prepared as described above were diluted 10-fold into assembly buffer containing 100 μM Thiazine red and incubated at 37° C. Aliquots were removed as a function of time up to 5 h post-dilution and assayed for total filament length. The disaggregation time course was fit to an exponential decay function to obtain $k_{app}$ as described previously [Kristofferson D, Karr T L, & Purich D L (1980) Dynamics of linear protein polymer disassembly. J Biol Chem 255(18):8567-8572; Necula M & Kuret J (2005) Site-specific pseudophosphorylation modulates the rate of tau filament dissociation. *FEBS Lett* 579(6):1453-1457; Zhong Q, Congdon E E, Nagaraja H N, & Kuret J (2012) Tau isoform composition influences the rate and extent of filament formation. *J Biol Chem*, incorporated by reference herein in their entireties]:

$$y = y_0 e^{-k_{app}t} \quad \text{Eq. 3}$$

where y is the filament length at time t, $y_0$ is filament length at time zero, and $k_{app}$ is the pseudo-first order rate constant for the process.

The association rate constant $k_{e+}$ was then determined from the relationship [Congdon E E, et al. (2008) Nucleation-dependent tau filament formation: the importance of dimerization and an estimation of elementary rate constants. J Biol Chem 283(20):13806-13816, incorporated by reference herein in its entirety]:

$$K_{crit} = k_{e-}/k_{e+} \quad \text{Eq. 4}$$

assuming a two state model (i.e., all tau was either monomeric or incorporated into filaments).

Aggregation Time Series

Aggregation lag times, defined as the time when the tangent to the point of maximum aggregation rate intersects the abscissa of the sigmoidal curve [Evans K C, Berger E P, Cho C G, Weisgraber K H, & Lansbury P T, Jr. (1995) Apolipoprotein E is a kinetic but not a thermodynamic inhibitor of amyloid formation: implications for the pathogenesis and treatment of Alzheimer disease. Proc Natl Acad Sci USA 92(3):763-767, incorporated by reference herein in its entirety], were obtained ±SE from each time series by Gompertz regression as described previously [Necula M & Kuret J (2004) A static laser light scattering assay for surfactant-induced tau fibrillization. Anal Biochem 333(2): 205-215, incorporated by reference herein in its entirety].

Statistical Analysis

Estimated kinetic parameters were assumed to resemble normally distributed random variables ($X_i$) with mean $\mu_i$ and known standard deviation $\sigma_t$. As a global test of the null hypothesis $H_0$ (i.e., that all compare $\mu_i$ values were the same), the statistic T based on the maximum likelihood ratio test principle [Rice J A (2007) Mathematical statistics and data analysis (Thomson Brooks/Cole, Belmont, Calif.) 3rd Ed pp xvi, 603, A663 p, incorporated by reference herein in its entirety] was calculated:

$$T = \sum_{i=1}^{k} w_i(X_i - \hat{\mu})^2 \quad \text{Eq. 5}$$

where k is the number of kinetic parameters being compared, T is the 1−α point of the Chi-square distribution having k−1 degrees of freedom, $w_i$=1/(↓i↑2, and (ˆ, the common mean under the null hypothesis, is the weighted sum of $X_i$:

$$\hat{\mu} = \frac{\sum_{i=1}^{k} w_i X_i}{\sum_{i=1}^{k} w_i} \quad \text{Eq. 6}$$

If $H_0$ were true, then the probability (p) of obtaining more extreme values of T than actually observed is $\alpha$.

For pairwise comparisons, the probability (p) of differences among parameters with SD was assessed by one-way ANOVA and Bonferroni post hoc multiple comparison test using Prism 5 (GraphPad Software, Inc., La Jolla, Calif.). The probability (p) of differences between kinetic parameters with SEE was assessed by z-test:

$$z = \frac{x_1 - x_2}{\sqrt{(S_{x1})^2 + (S_{x2})^2}} \quad \text{Eq. 7}$$

where $x_1 \pm S_{x1}$ and $x_2 \pm S_{x2}$ are the pair of estimates ±SE being compared, and z is the $1-\alpha$ point of the standard normal distribution using and JMP9.0 (SAS Institute, Cary, N.C.). The null hypothesis was rejected at $p<0.05$.

Results

Tau is Highly Methylated in Microtubule Binding Region of Pathologically Normal Brain.

Figure 5A:
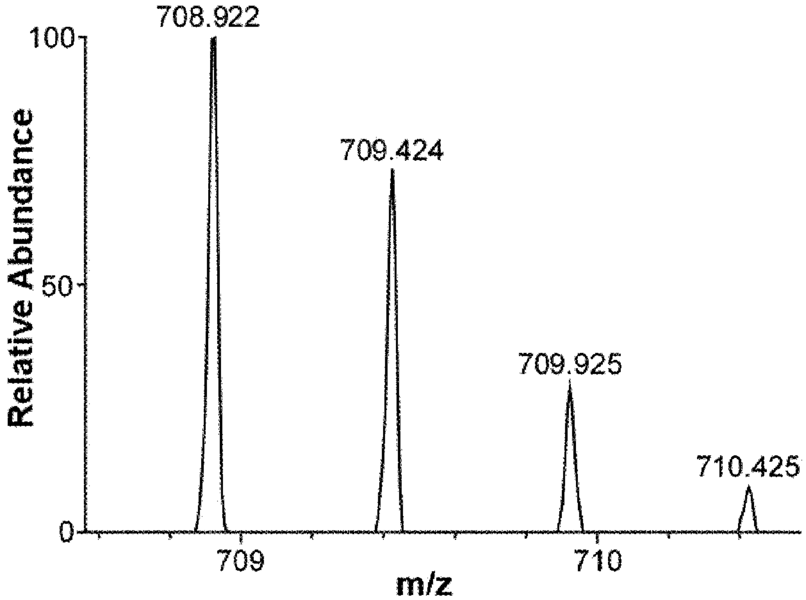
FIGS. 5A-5B show high mass accuracy determination of Lys311 dimethylation in human tau protein. Tau protein isolated from cognitively normal human brain was digested with trypsin and subjected to LC-MS/MS spectroscopy. MS data for peptide $_{306}$VQIVYK*PVDLSK$_{317}$ [SEQ. ID. NO. 1], where K* corresponds to dimethyl lysine, is shown, with FIG. 5A, isotopic envelope, and FIG. 5B, MS/MS spectrum and ion assignment. For this methylated peptide, the difference between expected and observed mass was 7.0 parts per million.
Figure 5B:
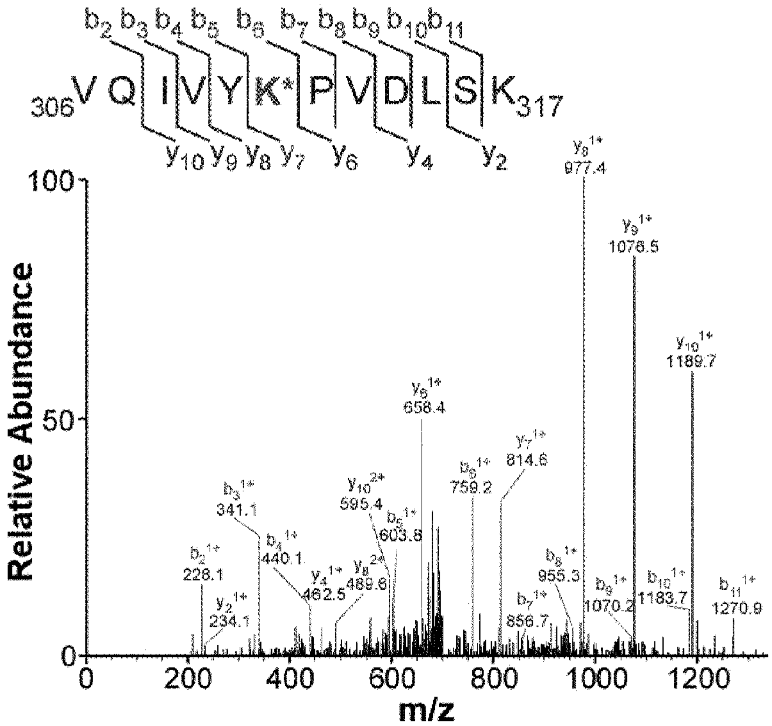
Figure 6B:
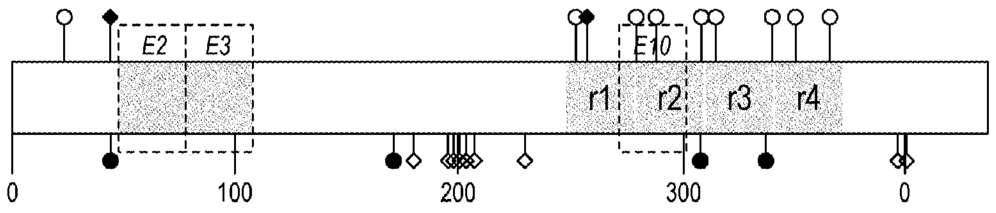

To identify sites of Lys modification in normal biology, tau was enriched from cognitively normal human brain. Because unlike most proteins, tau is heat-stable and acid-soluble, tau was enriched for by subtracting other proteins, then concentrated by TCA precipitation. Resuspended tau was digested in-gel with trypsin and analyzed by nanoflow liquid chromatography tandem mass spectrometry (LC-MS/MS). Resulting data were searched against a human database using Bioworks with the SEQUEST algorithm programmed to identify unmodified Lys residues along with sites of monomethylation (K+14), dimethylation (K+28), and trimethylation (K+42) as well as acetylation (also K+42). These search criteria identified 11 unique sites of modification with evidence of mono- and di-methylation (Table 5). An example of a mass spectrum identifying K311 at 7 ppm resolution as a site of dimethylation in normal tau is shown in FIG. 5. This site resides within the "PHF6" sequence, which has been shown to modulate the fibrillization rate of recombinant monomeric tau in vitro [von Bergen M, et al. (2000) Assembly of tau protein into Alzheimer paired helical filaments depends on a local sequence motif ((306)VQIVYK(311)) forming beta structure. Proc Natl Acad Sci USA 97(10):5129-5134; Iliev A I, Ganesan S, Bunt G, & Wouters F S (2006) Removal of pattern-breaking sequences in microtubule binding repeats produces instantaneous tau aggregation and toxicity. *J Biol Chem* 281(48): 37195-37204; Li W & Lee V M (2006) Characterization of two VQIXXK motifs for tau fibrillization in vitro. *Biochemistry* 45(51): 15692-15701, incorporated by reference herein in their entireties]. Additional sites were found in the N-terminal projection domain as well as within the MTBR (shown below amino acid sequence; FIG. 6). The presence of tau methylation in normal biology was further examined by enriching for tau from HEK293 cells that express human 2N4R tau under a tetracycline-inducible promoter [Bandyopadhyay B, Li G, Yin H, & Kuret J (2007) Tau aggregation and toxicity in a cell culture model of tauopathy. *J Biol Chem* 282(22):16454-16464, incorporated by reference herein in its entirety]. In this system, three sites of dimethylation were identified, two of which lie within the MTBR and overlap with sites found to be methylated in pathologically normal human brain (HEK; FIG. 6). Together, these data reveal that tau is a highly methylated protein in normal biology and decreased in the AD-state.

TABLE 5

Lys methylation sites identified on tau isolated from cognitively normal human brain. Trypsin in-gel digests of normal tau were analyzed by nanoflow LC-MS/MS and the data were searched against a human database using Bioworks with the SEQUEST algorithm. Bold = methylated Lys residues. Amino acid (aa) residues are based on 2N4R human. Abbreviations for tau domains: N = N-terminal projection domain; P = Pro-rich region; M = microtubule-binding domain; R1, R2, R3, R4 = repeat regions 1, 2, 3, and 4 respectively; C = C-terminal projection domain. Abbreviations for modifications are as follows: me1, monomethyl; me2, dimethyl.

| aa residues | Peptide | Methyl site | Modification | Tau domain |
|---|---|---|---|---|
| 24-44 | **K**DQGGYTMHQDQEDTDAGLK [SEQ. ID. NO. 2] | K24 | me2 | N |
| 25-44 | DQGGYTMHQDQEGDTDAGL**K** [SEQ. ID. NO. 3] | K44 | me1 | N |
| 243-257 | LQTAPVPMPDL**K**NVK [SEQ. ID. NO. 4] | K254 | me2 | M, R1 |
| 258-267 | S**K**IGSTENLK [SEQ. ID. NO. 5] | K259 | me1 | M, R1 |
| 281-290 | **K**LDLSNVQSK [SEQ. ID. NO. 6] | K281 | me2 | M, R2 |
| 281-290 | KLDLSNVQS**K** [SEQ. ID. NO. 7] | K290 | me2 | M, R2 |
| 306-317 | VQIVY**K**PVDLSK [SEQ. ID. NO. 1] | K311 | me2 | M, R3, PHF6 |

TABLE 5-continued

Lys methylation sites identified on tau isolated from cognitively normal human brain. Trypsin in-gel digests of normal tau were analyzed by nanoflow LC-MS/MS and the data were searched against a human database using Bioworks with the SEQUEST algorithm. Bold = methylated Lys residues. Amino acid (aa) residues are based on 2N4R human. Abbreviations for tau domains: N = N-terminal projection domain; P = Pro-rich region; M = microtubule-binding domain; R1, R2, R3, R4 = repeat regions 1, 2, 3, and 4 respectively; C = C-terminal projection domain. Abbreviations for modifications are as follows: me1, monomethyl; me2, dimethyl.

| aa residues | Peptide | Methyl site | Modification | Tau domain |
|---|---|---|---|---|
| 306-317 | VQIVYKPVDLS**K** [SEQ. ID. NO. 8] | K317 | me2 | M, R3 |
| 322-343 | CGSLGNIHHKPGGGQVEVKSE**K** [SEQ. ID. NO. 9] | K343 | me2 | M, R4 |
| 350-369 | VQS**K**IGSLDNITHVPGGGNK [SEQ. ID. NO. 10] | K353 | me2 | M, R4 |
| 354-369 | IGSLDNITHVPGGGN**K** [SEQ. ID. NO. 11] | K369 | me2 | M, R4 |

Preparation of Reductively Methylated Tau.

Figure 7A:
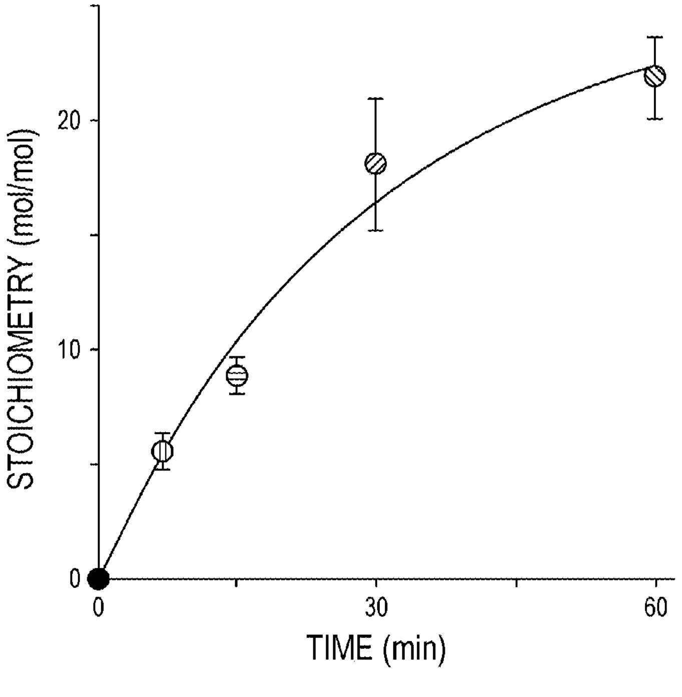
FIGS. 7A-7C show the effect of tau methylation on tau function and aggregation propensity. Purified recombinant human 2N4R tau protein was subjected to reductive methylation in the presence of formaldehyde for up to 60 min at room temperature. Aliquots of the reaction were removed as a function of time and subjected to spin dialysis to separate labeled tau from unincorporated formaldehyde.

To determine the effect of Lys methylation on tau function, methylated tau was prepared in vitro by reductive methylation (a well-characterized method for Lys-specific protein methylation [Means G E & Feeney R E (1968) Reductive alkylation of amino groups in proteins. Biochemistry 7(6):2192-2201; Borch R F, Bernstei. Md, & Durst H D (1971) Cyanohydridoborate Anion as a Selective Reducing Agent. J Am Chem Soc 93(12):2897, incorporated by reference herein in their entireties]). Rate and extent of tau methylation was monitored by incorporation of [$^{14}$C]-labeled methyl groups donated by [$^{14}$C]-formaldehyde during the reaction. A mol per mol stoichiometry of methyl group incorporation per mol tau was calculated by measuring the level of $^{14}$C incorporated into the known amount of tau. At 7, 15, 30 and 60 min, approximately 5, 10, 16, and 22 mol methyl were incorporated per mol tau, respectively (FIG. 7A). The sites of methyl group incorporation at 22 mol methyl per mol tau were determined by LC-MS/MS analysis (ReMe, FIG. 5). Most reductively methylated sites within the MTBR were also modified in cognitively normal biological samples, thus facilitating biochemical analysis of normal and pathological tau function, both of which are mediated by the MTBR.

Physiological Levels of Tau Methylation do not Inhibit Normal Functions of Tau.

Figure 7B:
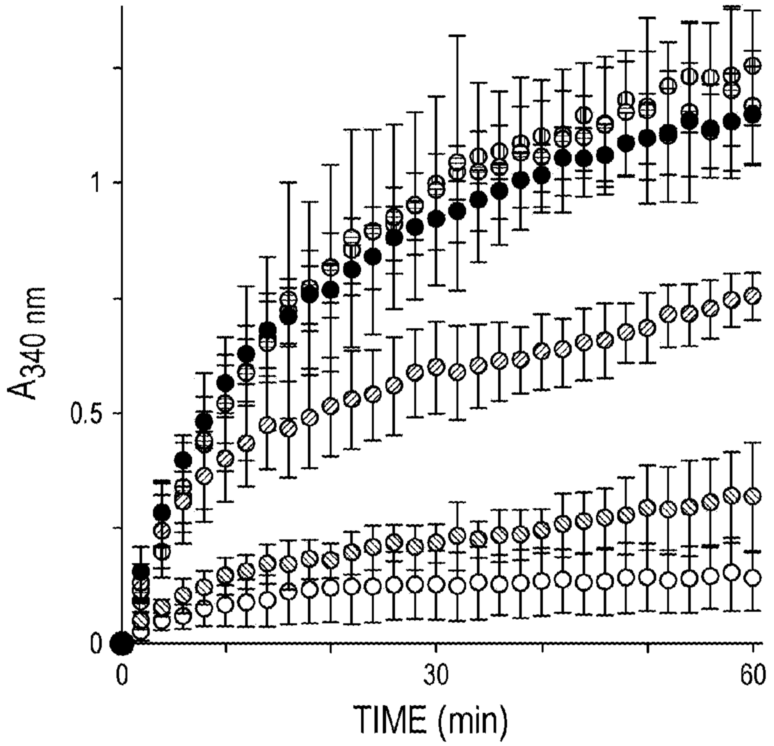
Figure 7C:
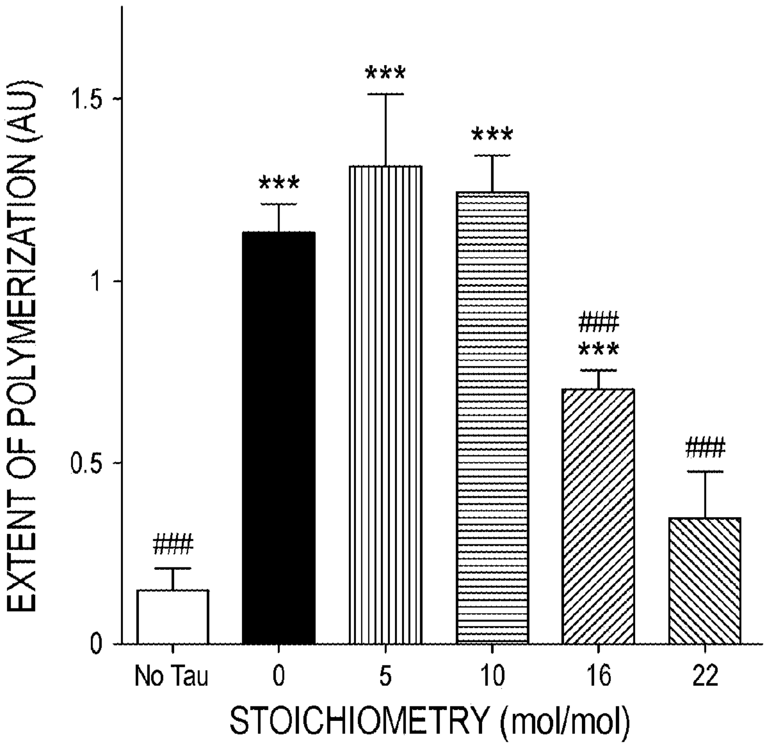

One of the normal functions of tau is the binding and stabilization of microtubules [Weingarten M D, Lockwood A H, Hwo S Y, & Kirschner M W (1975) A protein factor essential for microtubule assembly. Proc Natl Acad Sci USA 72(5):1858-1862; Witman G B, Cleveland D W, Weingarten M D, & Kirschner M W (1976) Tubulin requires tau for growth onto microtubule initiating sites. Proc Natl Acad Sci USA 73(11):4070-4074; Esmaeli-Azad B, McCarty J H, & Feinstein S C (1994) Sense and antisense transfection analysis of tau function: tau influences net microtubule assembly, neurite outgrowth and neuritic stability. J Cell Sci 107 (Pt 4):869-879; Drubin D G & Kirschner M W (1986) Tau protein function in living cells. J Cell Biol 103(6 Pt 2):2739-2746, incorporated by reference herein in their entireties]. Certain PTMs, including phosphorylation, can decrease the affinity of tau for microtubules and its ability to induce the polymerization of tubulin dimers into microtubules [Biernat J, Gustke N, Drewes G, Mandelkow E M, & Mandelkow E (1993) Phosphorylation of Ser262 strongly reduces binding of tau to microtubules: distinction between PHF-like immunoreactivity and microtubule binding. Neuron 11(1):153-163; Cho J H & Johnson G V (2003) Glycogen synthase kinase 3beta phosphorylates tau at both primed and unprimed sites. Differential impact on microtubule binding. J Biol Chem 278(1):187-193; Lu P J, Wulf G, Zhou X Z, Davies P, & Lu K P (1999) The prolyl isomerase Pin1 restores the function of Alzheimer-associated phosphorylated tau protein. Nature 399(6738):784-788; Yoshida H & Ihare Y (1993) Tau in paired helical filaments is functionally distinct from fetal tau: assembly incompetence of paired helical filament-tau. J Neurochem 61(3):1183-1186, incorporated by reference herein in their entireties]. To determine the effect of methylation on tau function in normal biology microtubule assembly was assayed in vitro. Either unmodified or reductively methylated tau was incubated at 37° C. with purified tubulin under conditions described in materials and methods, and the rate and extent of tubulin polymerization was measured by change in light absorbance at 340 nm. As shown in FIG. 7B, tubulin incubated at 37° C. in the absence of tau failed to appreciably polymerize. With the addition of unmodified tau, tubulin polymerized in an exponential fashion rising to a maximum of 1.14 absorbance units (AU) at a rate of 1.02E-3 s-1. Physiological levels of methylation (5-10 mol/mol) promoted tubulin polymerization identically. Only super-physiological levels of methylation (16-22 mol/mol) depressed the ability of tau to promote microtubule polymerization (FIG. 7C). Together, these data indicate that physiological levels of methylation do not inhibit the normal tau functions.

Lys Methylation Impedes Self-Aggregation of Tau.

Figure 8:
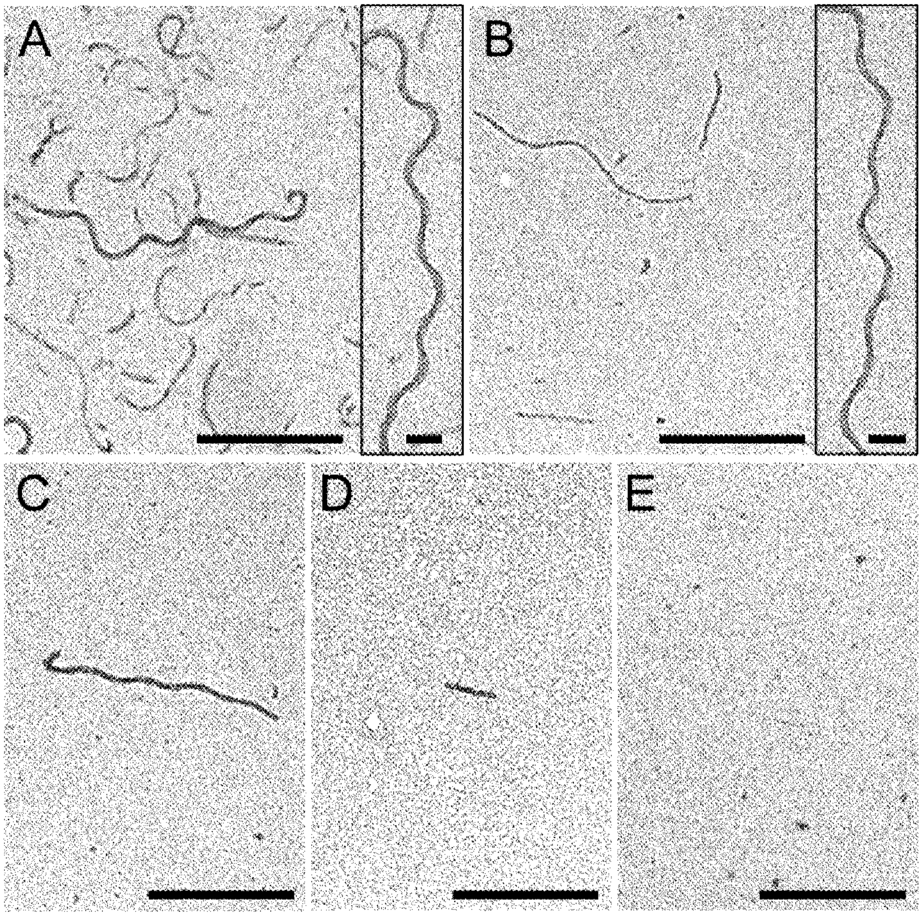
FIG. 8 shows that Lys methylation decreases tau aggregation propensity. Unmodified (A) or reductively methylated tau: 5 mol/mol (B), 10 mol/mol (C), 16 mol/mol (D), or 22 mol/mol methylation (D) was incubated at 2 μM in the presence of Thiazine red inducer for 18 h at 37° C., then assayed for filament formation by electron microscopy. (A-E) Scale bar=500 nm; Insets, Scale bar=100 nm. Tau methylation greatly depressed aggregation propensity, but not aggregate morphology under these conditions.

The self-aggregation of tau into paired helical filaments is a well-documented correlate of AD. To determine the effect of methylation on the pathological function of tau in self-aggregation, tau was incubated in the presence of Thiazine red aggregation inducer under near physiological conditions of pH, reducing conditions, and ionic strength. Under these conditions unmodified 2N4R tau forms twisted ribbons [Chirita C N, Congdon E E, Yin H, & Kuret J (2005) Triggers of full-length tau aggregation: a role for partially folded intermediates. Biochemistry 44(15):5862-5872, incorporated by reference herein in its entirety] with a mass-per-unit length similar to authentic brain-derived PHFs [Congdon E E, et al. (2008) Nucleation-dependent tau filament formation: the importance of dimerization and an estimation of elementary rate constants. J Biol Chem 283 (20):13806-13816, incorporated by reference herein in its entirety]. Tau aggregation was monitored by capturing images using transmission electron microscopy (TEM). Low magnification images demonstrate that while unmodified tau readily aggregates (FIG. 8A), methylation impairs aggregation propensity in a dose-dependent manner (FIG. 8B-E). High magnification images depict similar morphology of both unmodified and methylated tau filaments (FIG. 8A, B insets). These data indicate that methylated tau shares the fundamental aggregation characteristics of unmodified tau and can be studied at physiological bulk tau concentrations in the presence of Thiazine red inducer.

Figure 9A:
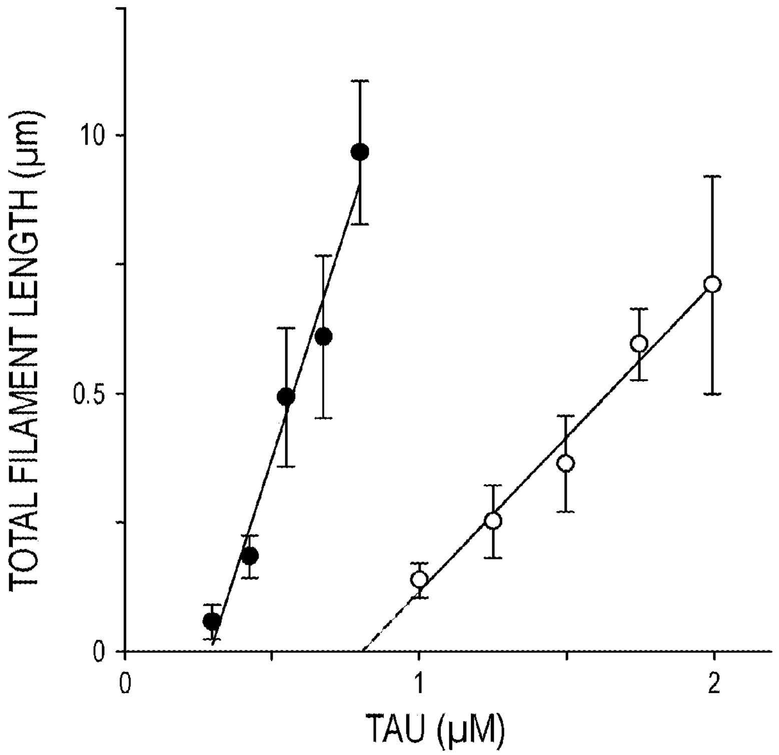
FIGS. 9A-9F generally show the mechanism through which Lys methylation decreases aggregation propensity.
Figure 9B:
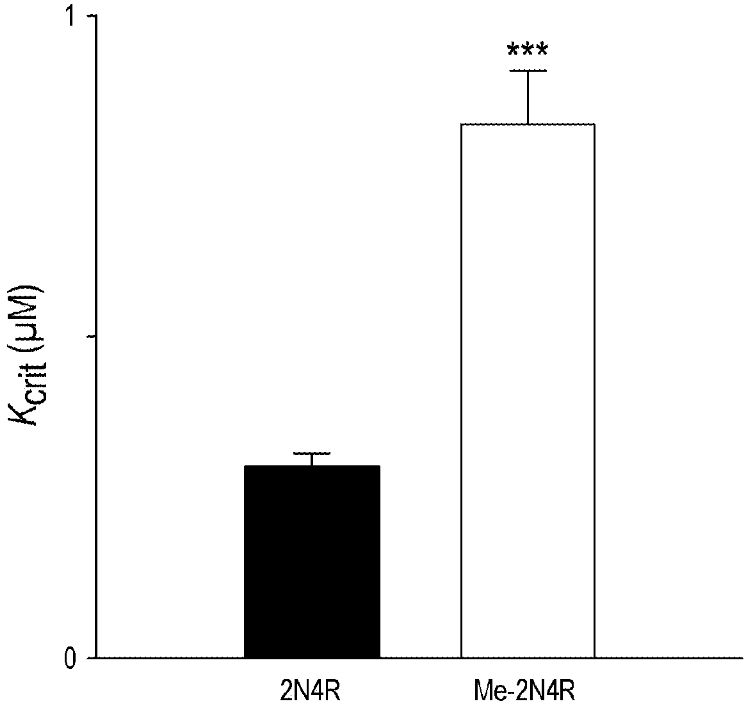

To quantify the effects of methylation on relative aggregation propensity, the critical concentration ($K_{crit}$) of unmodified or methylated tau was estimated in the presence of Thiazine red inducer. In nucleation-dependent reactions, $K_{crit}$ approximates the equilibrium dissociation constant for elongation, $K_e$ [Congdon E E, et al. (2008) Nucleation-dependent tau filament formation: the importance of dimerization and an estimation of elementary rate constants. J Biol Chem 283(20):13806-13816, incorporated by reference herein in its entirety]. $K_{crit}$ also represents the highest protein monomer concentration that does not support aggregation and is thus, estimated from the abscissa intercept of the tau concentration dependence plateau fibrillization (FIG. 9A). Results show that 5 mol/mol methyl incorporation increases the critical concentration nearly 3-fold relative to unmodified tau (FIG. 9B). These data indicate that Lys methylation depresses aggregation propensity, in part, by increasing the minimum concentration of tau needed to support fibril formation.

Figure 9C:
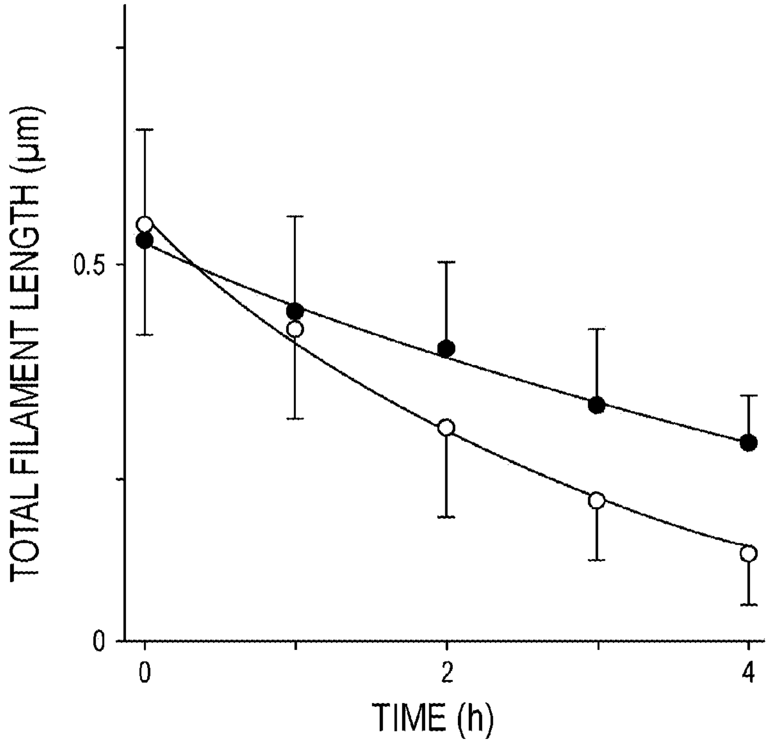
Figure 9D:
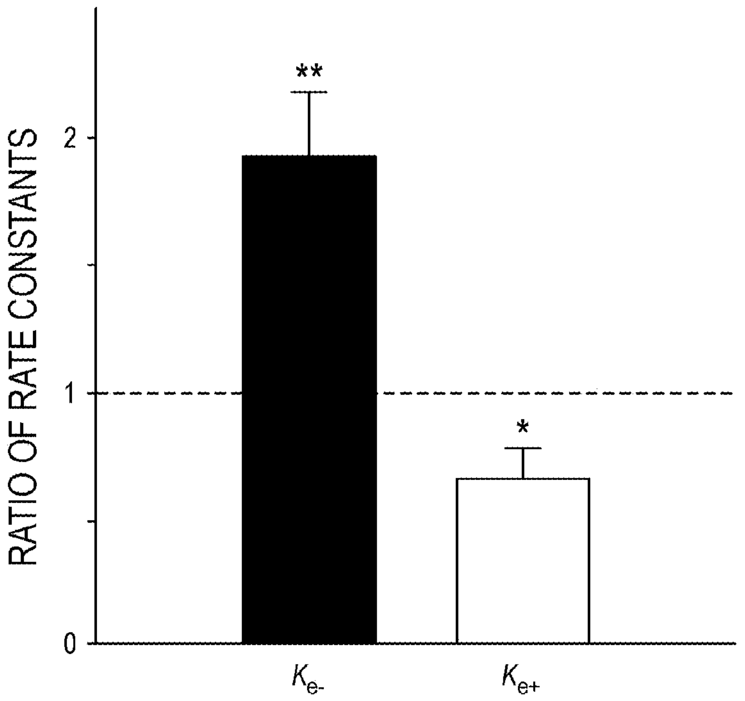

$K_{crit}$ approximates the ratio of dissociation ($k_{e-}$) and association ($k_{e+}$) rate constants for filament elongation (Eq. 4). Thus, modulation of Kcrit may result from changes in either filament stability ($k_{e-}$), efficiency of monomer association with filament ends ($k_{e+}$), or both. To differentiate between these possibilities, $k_{e-}$ was estimated for both unmodified and 5 mol/mol methylated tau by diluting pre-assembled filaments below their $K_{crit}$ and estimating the initial rate of filament shortening by electron microscopy. Loss of filament followed first-order kinetics as predicted for endwise depolymerization from a Poisson-like length distribution [Necula M & Kuret J (2005) Site-specific pseudophosphorylation modulates the rate of tau filament dissociation. *FEBS Lett* 579(6):1453-1457; Weingarten M D, Lockwood A H, Hwo S Y, & Kirschner M W (1975) A protein factor essential for microtubule assembly. *Proc Natl Acad Sci USA* 72(5):1858-1862, incorporated by reference herein in their entireties] (FIG. 9C). The dissociation elongation constant $k_{e-}$ was derived from the disaggregation rate of both unmodified and methylated tau using the established relationship between tau mass and filament length [Necula M & Kuret J (2005) Site-specific pseudophosphorylation modulates the rate of tau filament dissociation. FEBS Lett 579(6):1453-1457, incorporated by reference herein in its entirety]. Rate constant $k_{e+}$ was then calculated from estimates of $k_{e+}$ and $K_{crit}$ for each isoform using Eq. 4. Pairwise comparisons demonstrated that 5 mol/mol methylation increases $k_{e-}$ nearly 2-fold and decreases $k_{e+}$ about 1.5-fold (FIG. 9D), suggesting that both filament elongation and stability are decreased by methylation.

Figure 9E:
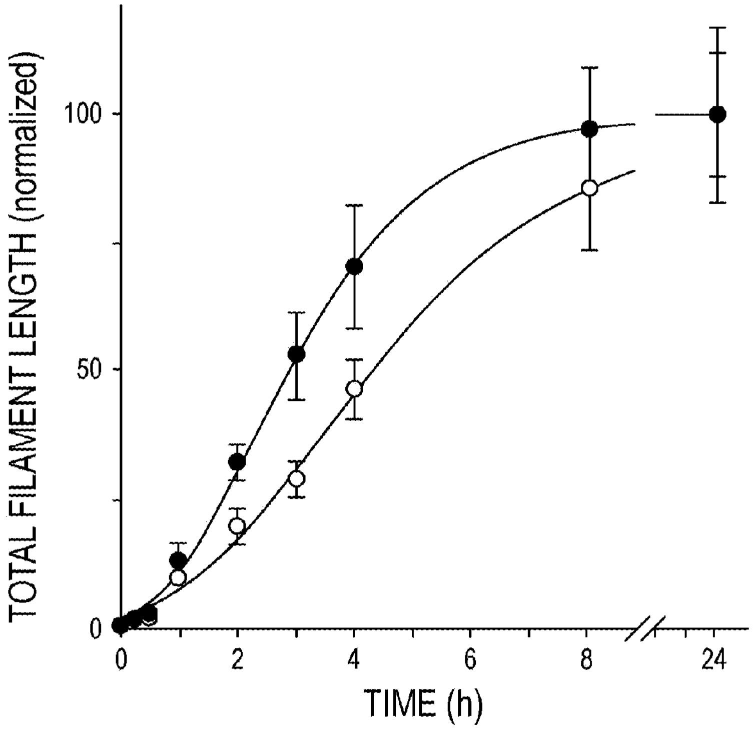
Figure 9F:
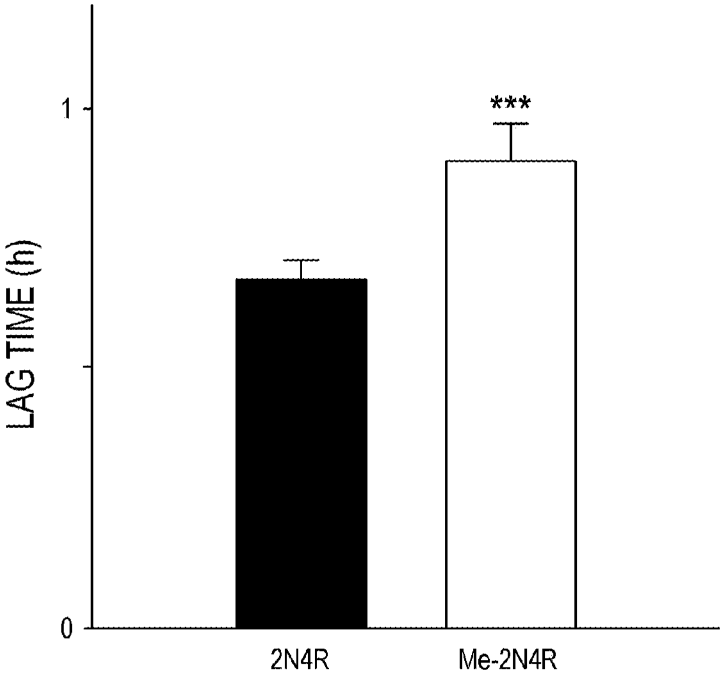

In the presence of Thiazine red inducer, the aggregation reaction is driven by rapid equilibrium of assembly-competent monomers with a thermodynamic nucleus, defined as the least stable species reversibly interconverted with monomer [Ferrone F (1999) Analysis of protein aggregation kinetics. Methods Enzymol 309:256-274, incorporated by reference herein in its entirety]. Since elongation can proceed efficiently only after the nucleus has formed, the rate of aggregation depends on nucleation rate as well as protein concentration and the rate of elongation ($k_{e-}$ and $K_{e+}$). In order to determine whether methylation affects nucleation rate, tau aggregation time course was quantified for both unmodified and 5 mol/mol methyl tau at constant supersaturation in the presence of Thiazine red. Under these conditions, differences in reaction rate primarily reflect differences in rates of nucleation and protein concentration [Fesce R, Benfenati F, Greengard P, & Valtorta F (1992) Effects of the neuronal phosphoprotein synapsin I on actin polymerization. II. Analytical interpretation of kinetic curves. J Biol Chem 267(16):11289-11299, incorporated by reference herein in its entirety]. Both reaction curves displayed lag, exponential growth, and equilibrium phases (FIG. 9E). Data was fit to a 3-parameter Gompertz growth function to calculate lag time, which vary inversely with nucleation rate [Evans K C, Berger E P, Cho C G, Weisgraber K H, & Lansbury P T, Jr. (1995) Apolipoprotein E is a kinetic but not a thermodynamic inhibitor of amyloid formation: implications for the pathogenesis and treatment of Alzheimer disease. Proc Natl Acad Sci USA 92(3):763-767, incorporated by reference herein in its entirety]. Data reveal that unmodified tau aggregated with a slight but significantly shorter lag time relative to methylated tau, despite being present at lower bulk concentrations (FIG. 9F). These data suggest that methylation modestly decelerates the nucleation phase of the tau aggregation reaction, though it has a greater effect on the rate of filament extension.

Discussion

In AD, neurofibrillary lesion formation is associated with changes in the tau PTM signature. The most well established tau PTM is phosphorylation, which increases 3- to 4-fold with disease onset; however phosphorylation does not exist in isolation. Rather, analyses have revealed a complex pattern of overlapping PTMs acting in a coordinated fashion to modulate tau activity. Recently we identified methylation as a novel tau PTM (14), and here we show that in contrast to phosphorylation, methylation is decreased in the disease state. We propose that tau PTMs, including phosphorylation and methylation, act in concert to affect both normal and pathological functions of tau.

Implications for Microtubule Dynamics

Microtubule binding and stabilization remain the most extensively studied functions of tau in normal biology, though whether or not these are vital is still debated. Studies have revealed that the majority of tau in the cell is bound to microtubules, and, as shown here and elsewhere, this microtubule binding activity promotes their assembly and stability. However, in cell culture and in vivo, tau colocalizes with those microtubules that are most dynamic [Kempf M, Clement A, Faissner A, Lee G, & Brandt R (1996) Tau binds to the distal axon early in development of polarity in a microtubule- and microfilament-dependent manner. J Neurosci 16(18):5583-5592; Fanara P, et al. (2010) Changes in microtubule turnover accompany synaptic plasticity and memory formation in response to contextual fear conditioning in mice. Neuroscience 168(1):167-178, incorporated by reference herein in their entireties]. Thus, microtubule stabilization, which can be compensated for by another microtubule-associated protein found in axons, MAP1B, may not be a critical function of tau in vivo. In fact, tau has numerous binding partners, including signaling molecules [Reynolds C H, et al. (2008) Phosphorylation regulates tau interactions with Src homology 3 domains of phosphatidylinositol 3-kinase, phospholipase Cgammal, Grb2, and Src family kinases. J Biol Chem 283(26):18177-18186, incorporated by reference herein in its entirety], cytoskeletal elements [Fulga T A, et al. (2007) Abnormal bundling and accumulation of F-actin mediates tau-induced neuronal degeneration in vivo. Nat Cell Biol 9(2):139-148, incorporated by reference herein in its entirety], and lipids [Reynolds C H, et al. (2008) Phosphorylation regulates tau interactions with Src homology 3 domains of phosphatidylinositol 3-kinase, phospholipase Cgammal, Grb2, and Src family kinases. J Biol Chem 283(26):18177-18186; Hwang S C, Jhon D Y, Bae Y S, Kim J H, & Rhee S G (1996) Activation of phospholipase C-gamma by the concerted action of tau proteins and arachidonic acid. J Biol Chem 271(31):18342-18349; Jenkins S M & Johnson G V (1998) Tau complexes with phospholipase C-gamma in situ. Neuroreport 9(1):67-71, incorporated by reference herein in their entireties], suggesting that it is a multifunctional protein.

A prominent theory suggests that disease may be caused by loss of tau function due to hyperphosphorylation and sequestration of soluble tau. However, considering that hyperphosphorylation occurs in fetal development [Seubert P, et al. (1995) Detection of phosphorylated Ser262 in fetal tau, adult tau, and paired helical filament tau. J Biol Chem 270(32):18917-18922, incorporated by reference herein in its entirety] and hibernation [Arendt T, et al. (2003) Reversible paired helical filament-like phosphorylation of tau is an adaptive process associated with neuronal plasticity in hibernating animals. J. Neurosci. 23(18):6972-6981, incorporated by reference herein in its entirety] without filamentous aggregation, hyperphosphorylation of tau per se does not cause neurodegeneration. Furthermore, several mouse lines with MAPT knocked out have been developed, and for the most part, exhibit normal behavior throughout most of their lives [Roberson E D, et al. (2007) Reducing endogenous tau ameliorates amyloid beta-induced deficits in an Alzheimer's disease mouse model. Science 316(5825):750-754; Dawson H N, et al. (2010) Loss of tau elicits axonal degeneration in a mouse model of Alzheimer's disease. Neuroscience 169 (1):516-531; Ittner L M, et al. (2010) Dendritic function of tau mediates amyloid-beta toxicity in Alzheimer's disease mouse models. Cell 142(3):387-397; Ikegami S, Harada A, & Hirokawa N (2000) Muscle weakness, hyperactivity, and impairment in fear conditioning in tau-deficient mice. Neurosci Lett 279(3):129-132, incorporated by reference herein in their entireties].

Provided that the dissociation equilibrium constant for binding remains lower than the concentration of available tau binding sites on the microtubules, small changes in affinity may not appreciably affect free tau concentrations. For example, wild type or tauopathic mutant tau microinjected at physiological concentrations into Michigan Cancer Foundation 7 (MCF7) cells colocalize with tubulin similarly [Bunker J M, Kamath K, Wilson L, Jordan M A, & Feinstein S C (2006) FTDP-17 mutations compromise the ability of tau to regulate microtubule dynamics in cells. J Biol Chem 281(17):11856-11863, incorporated by reference herein in its entirety]. Therefore, it is unlikely that any loss of tau function caused by methylation would significantly impact neuronal health, and differences in dynamics most likely reflect intrinsic mechanistic differences rather than differential binding. Rather, tau methylation may exert its benefit by potently inhibiting tau aggregation into pathological filaments.

Implications for Aggregation Mechanism

Figure 10:
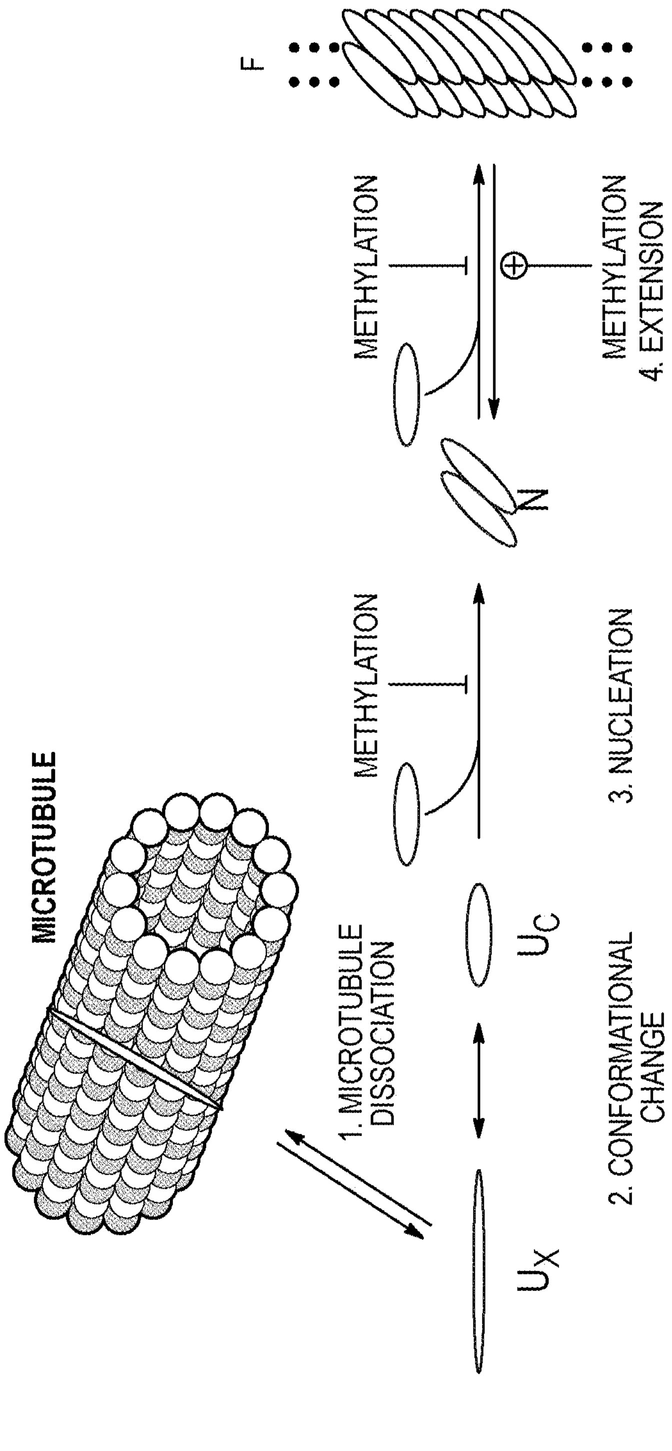
FIG. 10 is a schematic showing that methylation inhibits filament formation through multiple points in the pathway with its greatest effect being the combination of decreased extension and increased disassembly of the filament.

Tau aggregation within cells is a complex process that is modulated by both intrinsic aggregation propensity and modulation by other cellular factors. We have proposed that the tau aggregation pathway involves four principal steps that must be overcome in order for filamentous aggregates to accumulate in disease [Congdon E E, et al. (2008) Nucleation-dependent tau filament formation: the importance of dimerization and an estimation of elementary rate constants. J Biol Chem 283(20):13806-13816, incorporated by reference herein in its entirety] (FIG. 10). First, the concentration of cytoplasmic free tau must rise to exceed the minimal tau concentration necessary to support aggregation. This can be accomplished by increased MAPT expression, decreased tau degradation, or decreased affinity of tau for microtubules. The potential role of tau methylation in protein degradation is intriguing considering that methylation and ubiquitylation compete for Lys residue site occupancy (FIG. 6); however, the actual contribution of tau methylation to protein degradation is currently unknown. Considering that we show here that tau methylation is high in normal biology, one might speculate that methylation does not depress protein degradation, which would seem to promote aggregation. However, it is interesting that two sites of methylation in normal human brain (K254 and K311) are found to be ubiquitylated in AD brain. The dynamic modulation of these sites and their relative function in health and disease are still to be completed.

The second step of the tau aggregation pathway involves a conformational change to an assembly competent state (FIG. 10). Because high concentrations (up to 100 μM) of free tau alone are insufficient to support aggregation in vitro [Ko L W, DeTure M, Sahara N, Chihab R, & Yen S H (2002) Cellular models for tau filament assembly. J Mol Neurosci 19(3):311-316, incorporated by reference herein in its entirety], this is proposed to be a barrier to aggregation. Phosphorylation of tau is thought to induce local polyproline II helix conformation [Bielska A A & Zondlo N J (2006) Hyperphosphorylation of tau induces local polyproline II helix. Biochemistry 45(17):5527-5537, incorporated by reference herein in its entirety], and assist in overcoming the resistance of monomeric tau to aggregate. Although the conformational changes associated with methylation of tau are unknown, methylation of other proteins does not appear to significantly alter protein secondary structure [Rypniewski W R, Holden H M, & Rayment I (1993) Structural consequences of reductive methylation of lysine residues in hen egg white lysozyme: an X-ray analysis at 1.8-A resolution. Biochemistry 32(37):9851-9858, incorporated by reference herein in its entirety]. However, increasing methyl stoichiometry, either by the number of sites or the nature of methylation (i.e., mono, di, or tri), increases a protein's hydrophobicity [Taverna S D, Li H, Ruthenburg A J, Allis C D, & Patel D J (2007) How chromatin-binding modules interpret histone modifications: lessons from professional pocket pickers. Nat Struct Mol Biol 14(11):1025-1040, incorporated by reference herein in its entirety]. It has been hypothesized that the unfolded nature of tau can be attributed mostly to the lack of hydrophobicity and that aggregation is largely determined by ionic interactions [Jeganathan S, von Bergen M, Mandelkow E M, & Mandelkow E (2008) The natively unfolded character of tau and its aggregation to Alzheimer-like paired helical filaments. Biochemistry 47(40):10526-10539, incorporated by reference herein in its entirety]. Therefore, it is possible that methylation inhibits tau aggregation by stabilizing it in a conformation resistant to aggregation.

Once aggregation-competent conformations are adopted, the rate-limiting step in filament formation becomes dimerization [Congdon E E, et al. (2008) Nucleation-dependent tau filament formation: the importance of dimerization and an estimation of elementary rate constants. J Biol Chem 283(20):13806-13816, incorporated by reference herein in its entirety], which is energetically disfavored at physiological tau concentrations, and therefore, a third point of control (FIG. 10). Reductive methylation of tau decreases aggregation propensity consistent with a slight deceleration of filament nucleation rate. The final step in tau fibrillization is mediated by filament extension. Although not a rate-limiting step, equilibria at filament ends dictate the minimal concentration of tau required to support aggregation. Reductive methylation of tau significantly decreased filament elongation by decreasing the rate at which monomers associate with filament ends as well as increasing the rate at which monomers dissociate with filament ends. Together, these results indicate that reductive methylation of tau acts in opposition to phosphorylation and certain tauopathic mutations, which promote tau filament formation.

In summary, these data suggest that tau is highly methylated in normal biology and could depress neurofibrillary lesion accrual though the inhibition of tau filament formation. This work establishes the role of methylation as a modulator of tau protein, and emphasizes the overlapping and sometimes contradicting PTM signature that act in concert to regulate both normal and pathological functions of tau. Furthermore, this suggests tau methylation may be a novel target for pharmacological efforts in disease-modifying treatments of tauopathies.

While the present invention has been disclosed by reference to the details of preferred embodiments of the invention, it is to be understood that the disclosure is intended as an illustrative rather than in a limiting sense, as it is contemplated that modifications will readily occur to those skilled in the art, within the spirit of the invention and the scope of the amended claims.

The invention claimed is:

1. A method comprising:

a. obtaining a test biological sample from an individual, the test biological sample being chosen from cerebrospinal fluid, blood, serum, and plasma;

b. quantifying the amounts of a methylated tau protein in the test biological sample obtained in step a, said methylation occurring on one or more lysine residues, wherein said quantifying of said methylated tau protein is achieved via use of an antibody to a methylated peptide derived from tau protein;

c. comparing the amounts of methylated tau protein in the test biological sample with the amounts present in a control biological sample from a subject without Alzheimer's disease;

d. diagnosing Alzheimer's disease, or predisposition thereto, based on a difference in the amount of the methylated tau protein in the test biological sample as compared to the control biological sample; and e. administering to the individual a composition chosen from:

i. a composition having at least one antigenic tau peptide linked to an immunogenic carrier, wherein the antigenic tau peptide is monomethylated on one or more lysines, and wherein the one or more monomethylated lysines are numbered according to the human tau isoform with NCBI accession number NP_005901and include one or more of the following residues: 24, 44, 163, 174, 180, 254, 267, 281, 290, 311, 317, 340, 353, 369, and 395; and ii. a composition having at least one antibody to an antigenic tau peptide including at least one monomethylated lysine epitope numbered according to the human tau isoform with NCBI accession number NP_005901and including one or more of the following residues: 24, 44, 163, 174, 180, 254, 267, 281, 290, 311, 317, 340, 353, 369, and 395.

2. The method of claim 1, further comprising comparing and/or detecting a change in the level of the methylated tau protein present in samples taken on two or more occasions.

3. The method of claim 1, further comprising comparing the amount of the methylated tau protein present in said test biological sample with more than one control sample.

4. The method of claim 1, wherein the biological sample is an extract, purification, or dilution from the sample chosen from cerebrospinal fluid, blood, serum, and plasma.

* * * * *

UNITED STATES PATENT AND TRADEMARK OFFICE

CERTIFICATE OF CORRECTION

PATENT NO. : 9,738,709 B2
APPLICATION NO. : 14/353069
DATED : August 22, 2017
INVENTOR(S) : Kuret et al.

It is certified that error appears in the above-identified patent and that said Letters Patent is hereby corrected as shown below:

In the Specification

Column 1, Lines 24-28 replace the Government Support Clause with:
--This invention was made with government support under grant number AG014452 awarded by the National Institutes of Health. The government has certain rights in the invention.--

Signed and Sealed this
Fifteenth Day of September, 2020

Andrei Iancu
*Director of the United States Patent and Trademark Office*